(12) United States Patent
Matsuyama

(10) Patent No.: US 8,324,170 B2
(45) Date of Patent: Dec. 4, 2012

(54) INTERFERON GAMMA RECEPTOR BETA CHAIN COMPOSITIONS AND METHODS OF INHIBITING APOPTOSIS

(75) Inventor: Shigemi Matsuyama, Beachwood, OH (US)

(73) Assignee: Case Western Reserve University, Cleveland, OH (US)

( * ) Notice: Subject to any disclaimer, the term of this patent is extended or adjusted under 35 U.S.C. 154(b) by 48 days.

(21) Appl. No.: 12/853,122

(22) Filed: Aug. 9, 2010

(65) Prior Publication Data

US 2011/0034395 A1 Feb. 10, 2011

Related U.S. Application Data

(60) Provisional application No. 61/232,050, filed on Aug. 7, 2009.

(51) Int. Cl.
| | |
|---|---|
| *A61K 38/08* | (2006.01) |
| *A61K 38/04* | (2006.01) |
| *A61K 38/16* | (2006.01) |
| *C07K 14/715* | (2006.01) |

(52) U.S. Cl. ............... 514/18.9; 514/21.3; 514/21.4; 514/21.5; 514/21.6; 514/21.7; 514/21.8

(58) Field of Classification Search ............... None
See application file for complete search history.

(56) References Cited

U.S. PATENT DOCUMENTS

| 7,314,866 B2 * | 1/2008 | Matsuyama |
| 8,183,342 B2 * | 5/2012 | Matsuyama |
| 2011/0038854 A1 * | 2/2011 | Kotenko |

FOREIGN PATENT DOCUMENTS

WO  WO 02088163 A1 * 11/2002

OTHER PUBLICATIONS

Geomz et al., The C-terimus of interferon gamma receptor beta chain (IFNgR2) has antiapoptotic activity as a Bax inhibitor, Cancer Biol. & Ther. 8(18):1771-1786, Sep. 15, 2009.*
Farrar et al. Identifcation of a functionally important sequence in the C terminus of the interferon-gamma receptor, Proc. Natl. Acad. Sci, USA, 89:11706-11710, Dec. 1992.*
Bernabei et al., Inteferon-gamma receptor 2 expression as the deciding factor in human T, B, and myeloid cell proliferation or death, J. Leuk. Biol. 70:950-960, Dec. 2001.*

* cited by examiner

*Primary Examiner* — Claire Kaufman
(74) *Attorney, Agent, or Firm* — Tarolli, Sundheim, Covell & Tummino LLP

(57) ABSTRACT

A method of inhibiting apoptosis in a cell includes administering to a cell an effective amount of a cell penetrating peptide (CPP), wherein the CPP consists of about 5 to about 41 amino acids and is substantially homologous to a portion of the C-terminal region of IFNγR2.

18 Claims, 10 Drawing Sheets

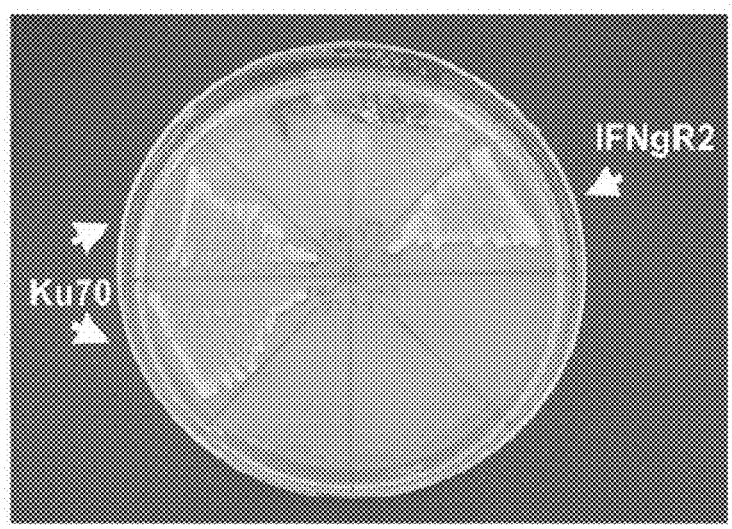
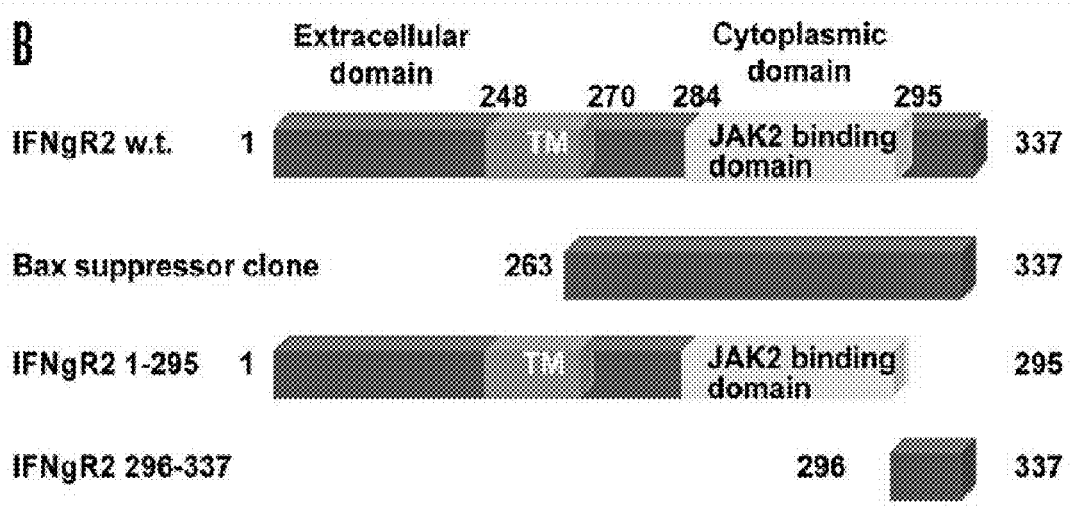
Fig. 1A-B

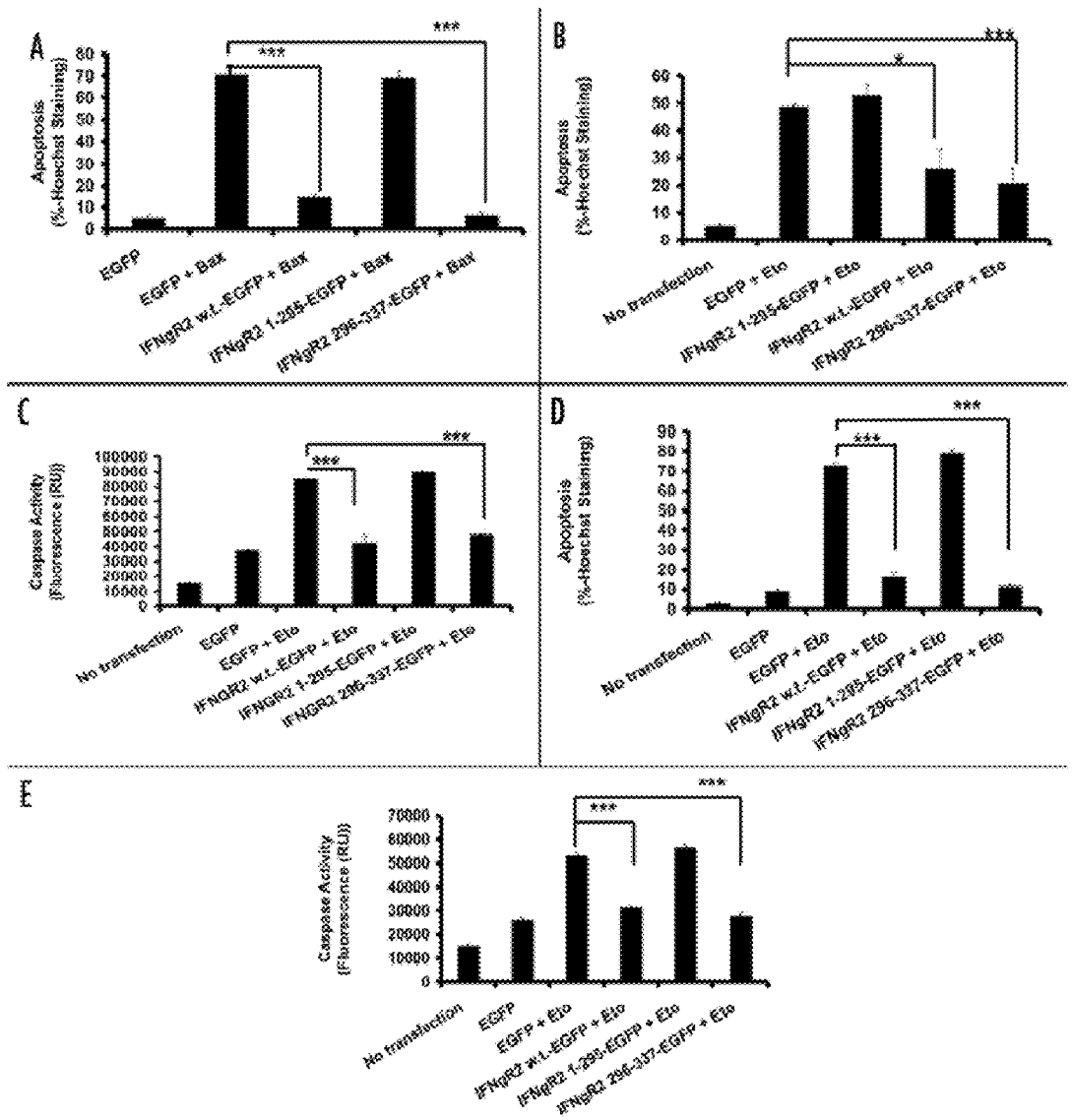
Fig. 2A-E

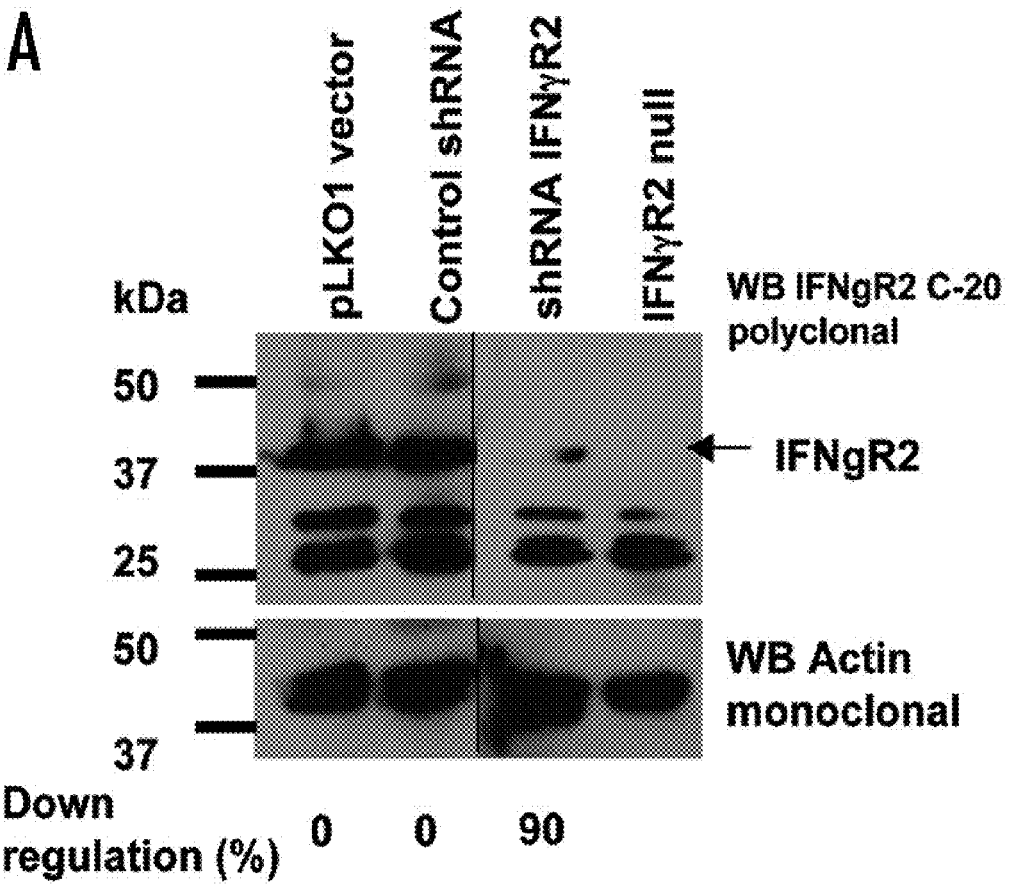
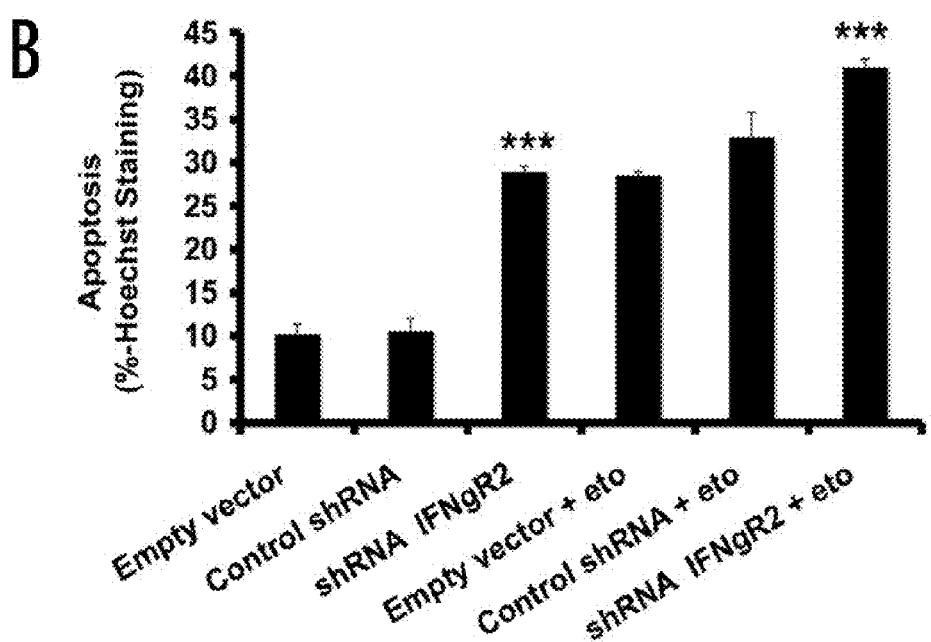
Fig. 3A-B

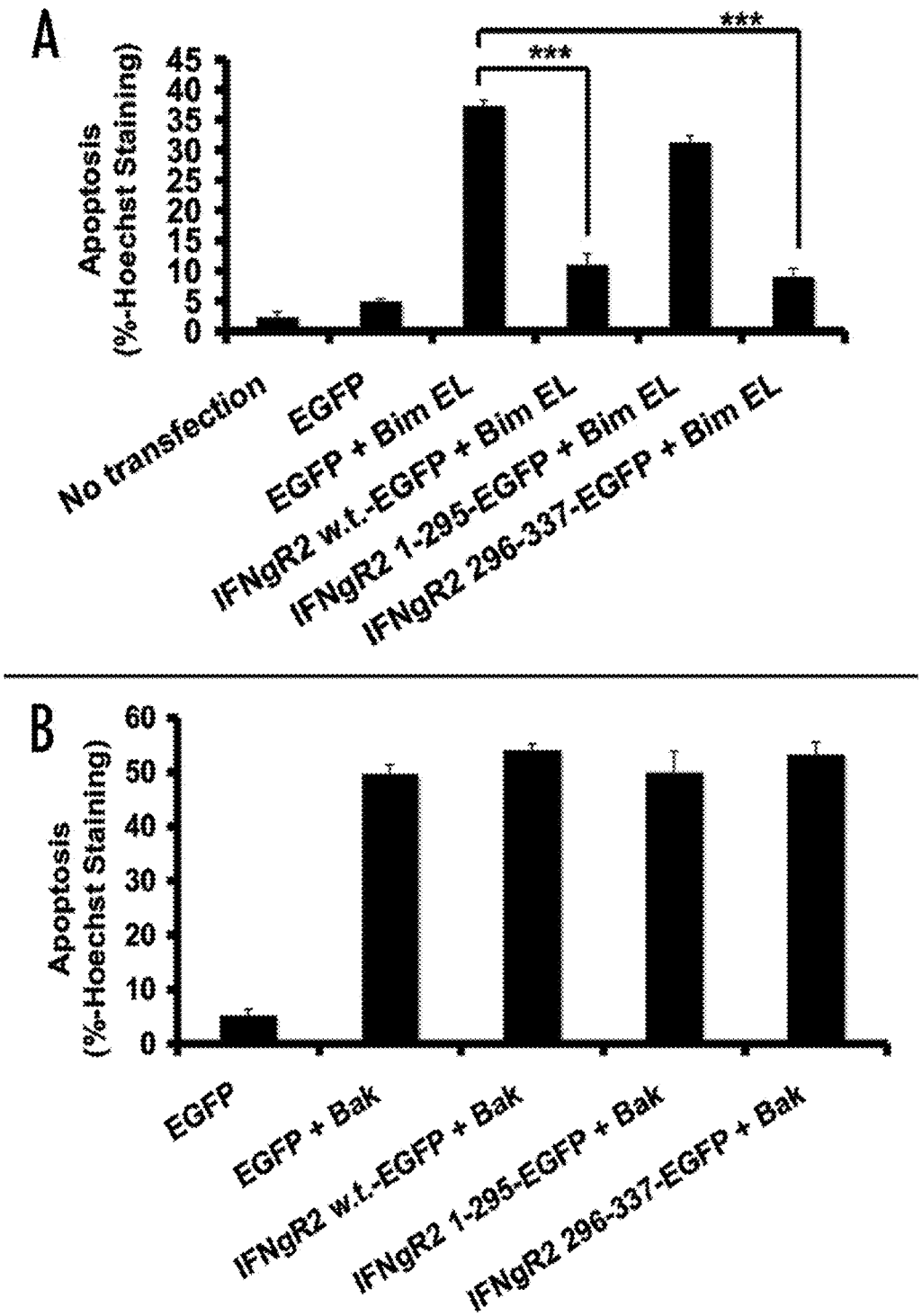
Fig. 4A-B

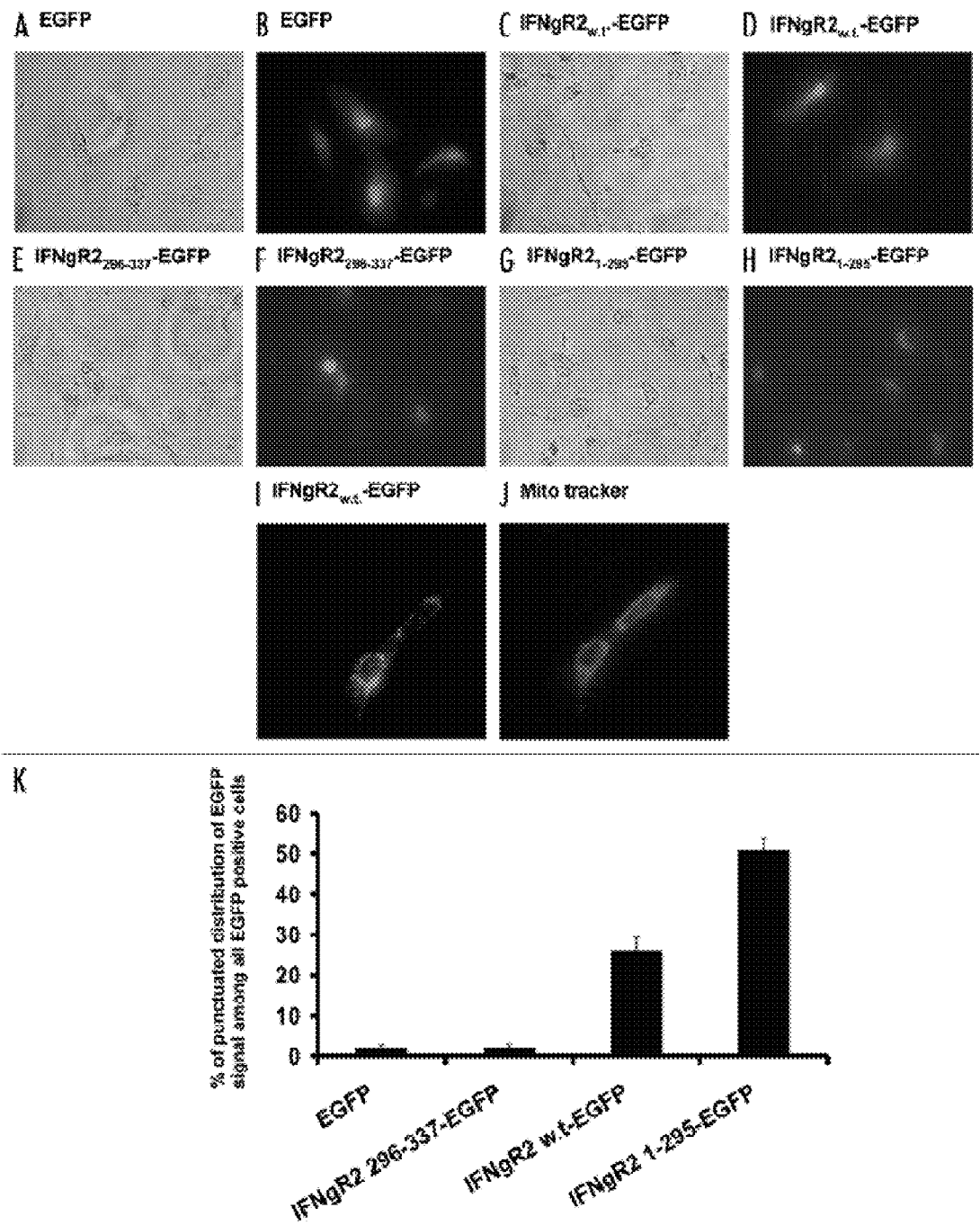
Fig. 5A-K

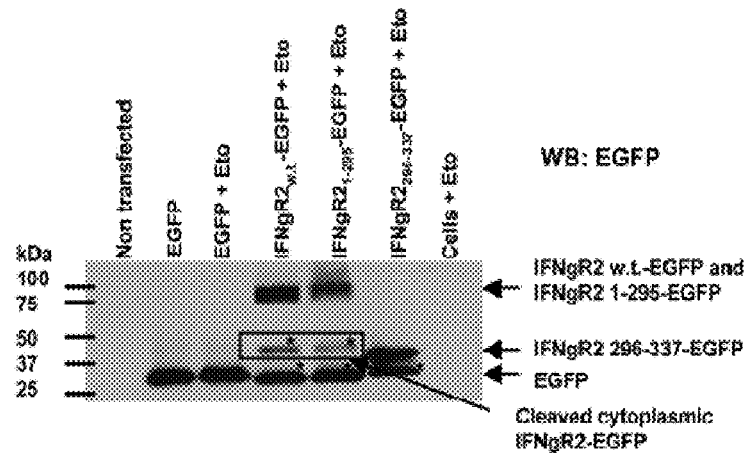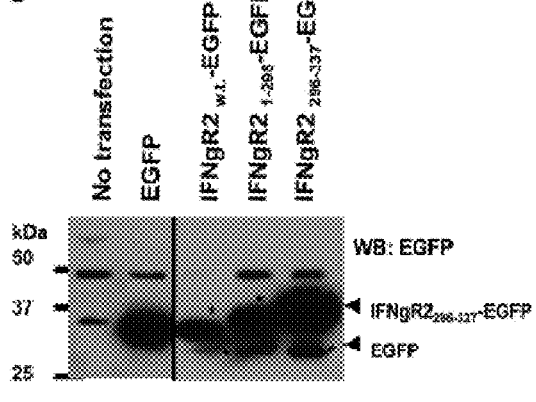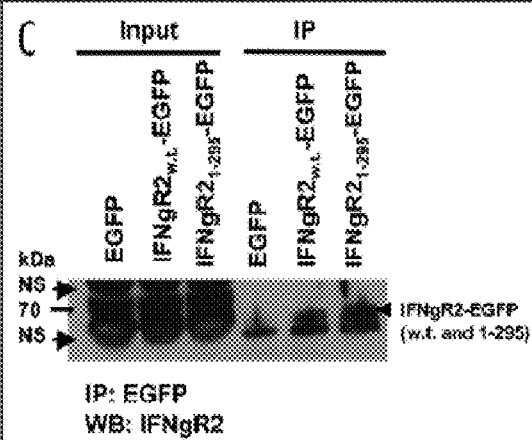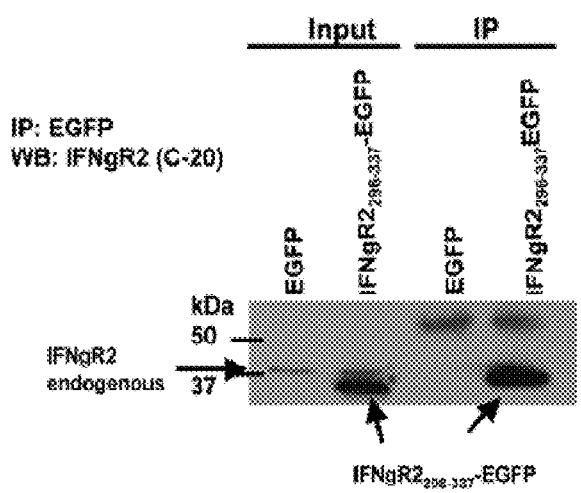
Fig. 6A-D

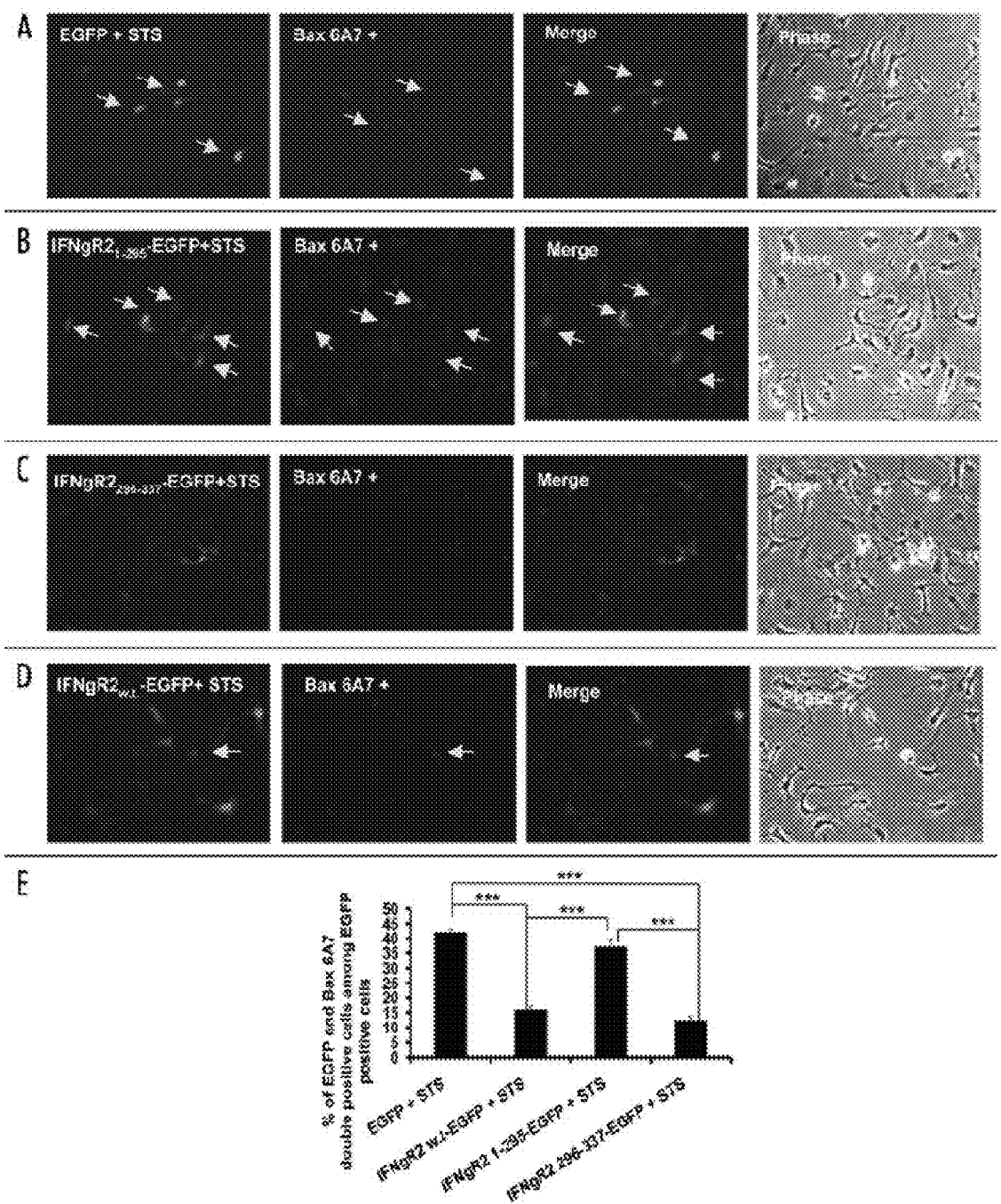
Fig. 7A-E

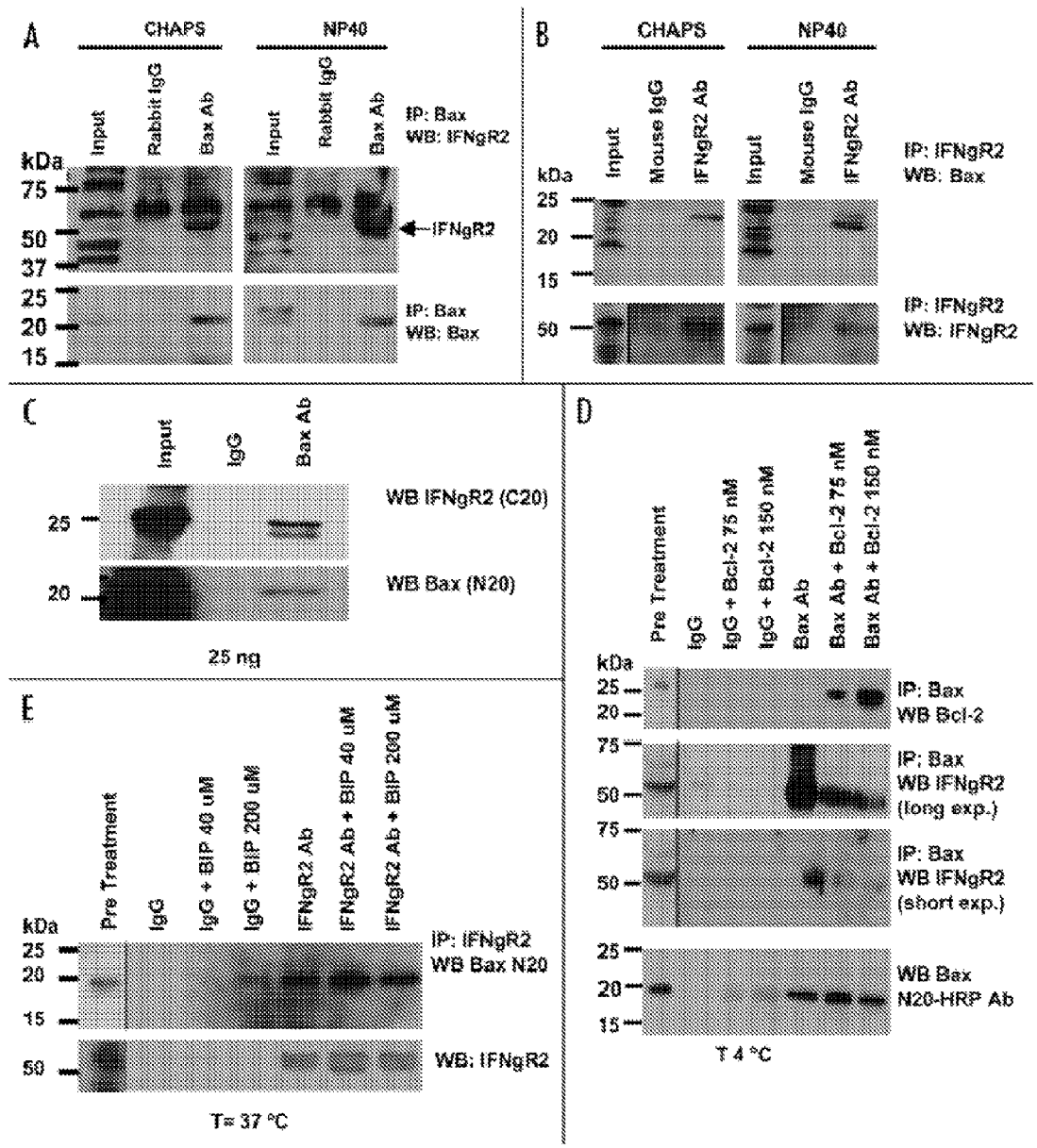
Figs. 8A-E

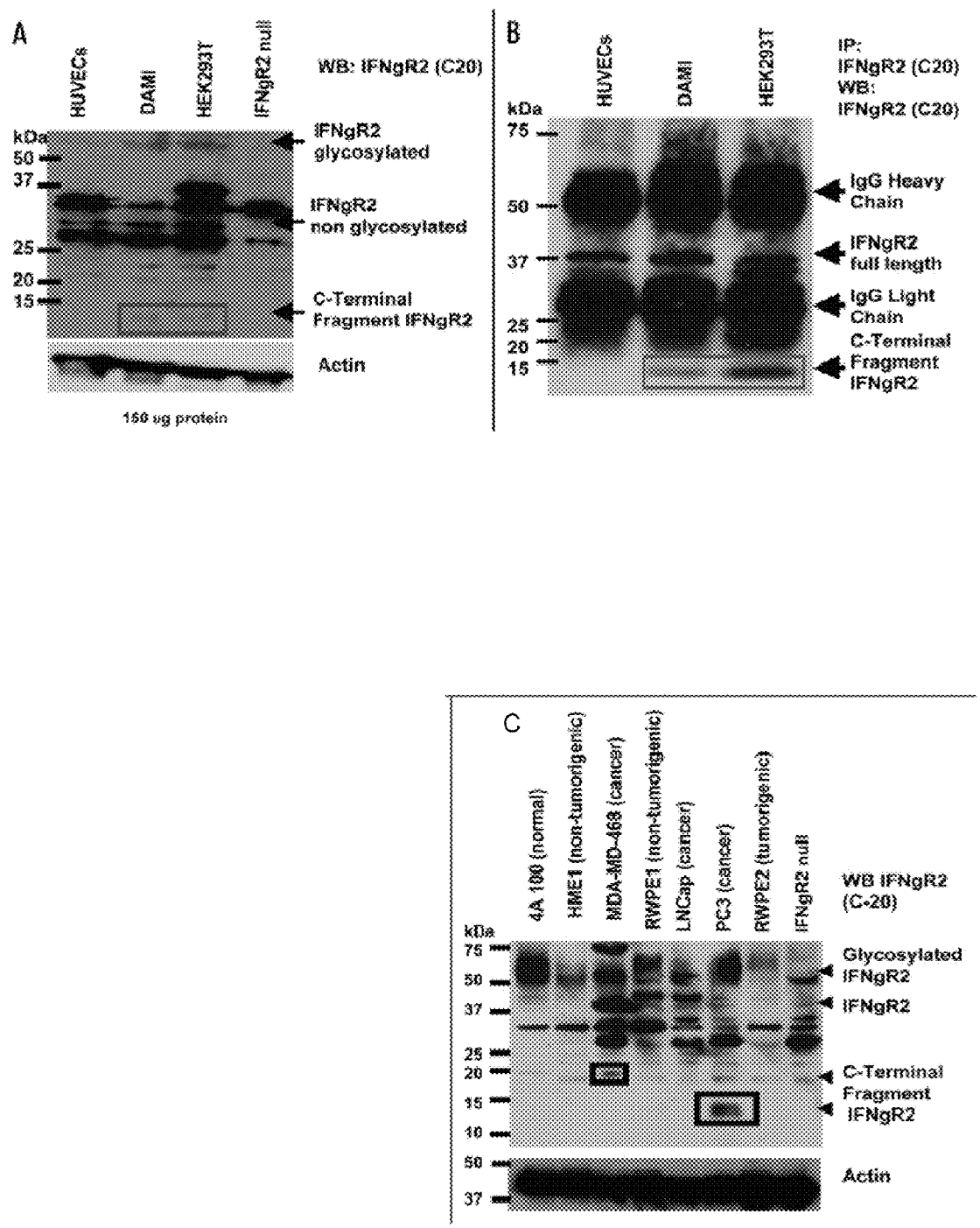
Figs. 9A-C

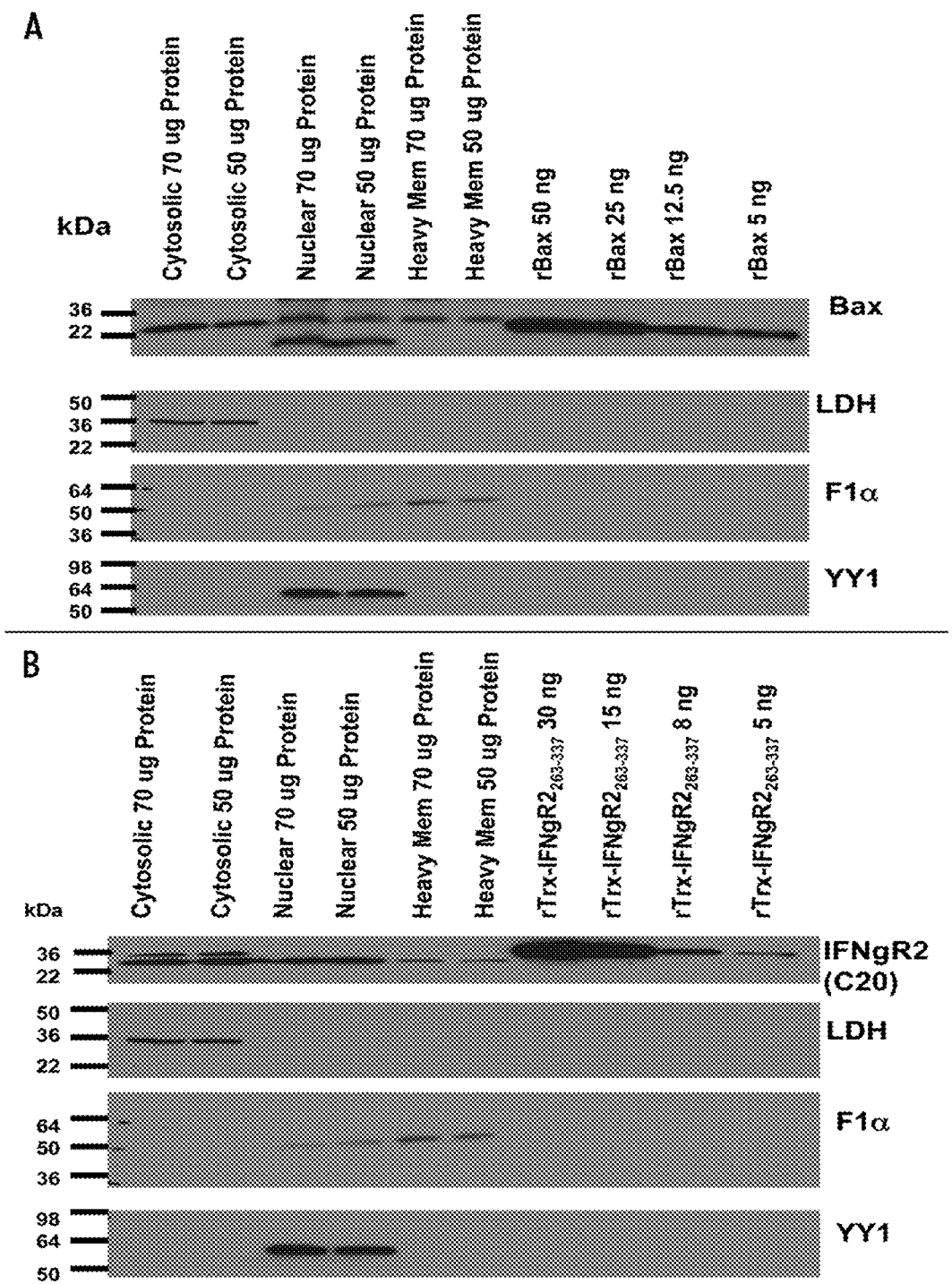
Fig. 10A-B

SEQUENCE LISTING

```
<160> NUMBER OF SEQ ID NOS: 13

<210> SEQ ID NO 1
<211> LENGTH: 42
<212> TYPE: PRT
<213> ORGANISM: Homo sapiens

<400> SEQUENCE: 1

Lys Asp Pro Thr Gln Pro Ile Leu Glu Ala Leu Asp Lys Asp Ser Ser
1               5                   10                  15

Pro Lys Asp Asp Val Trp Asp Ser Val Ser Ile Ile Ser Phe Pro Glu
            20                  25                  30

Lys Glu Gln Glu Asp Val Leu Gln Thr Leu
        35                  40

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

Pro Ile Leu Glu Ala
1               5

<210> SEQ ID NO 3
<211> LENGTH: 337
<212> TYPE: PRT
<213> ORGANISM: Homo sapiens

<400> SEQUENCE: 3

Met Arg Pro Thr Leu Leu Trp Ser Leu Leu Leu Leu Leu Gly Val Phe
```

```
      1               5                  10                 15
Ala Ala Ala Ala Ala Ala Pro Pro Asp Pro Leu Ser Gln Leu Pro Ala
                    20                  25                 30

Pro Gln His Pro Lys Ile Arg Leu Tyr Asn Ala Glu Gln Val Leu Ser
                    35                  40                 45

Trp Glu Pro Val Ala Leu Ser Asn Ser Thr Arg Pro Val Val Tyr Gln
        50                  55                  60

Val Gln Phe Lys Tyr Thr Asp Ser Lys Trp Phe Thr Ala Asp Ile Met
 65                      70                  75                 80

Ser Ile Gly Val Asn Cys Thr Gln Ile Thr Ala Thr Glu Cys Asp Phe
                    85                  90                  95

Thr Ala Ala Ser Pro Ser Ala Gly Phe Pro Met Asp Phe Asn Val Thr
                   100                 105                 110

Leu Arg Leu Arg Ala Glu Leu Gly Ala Leu His Ser Ala Trp Val Thr
                   115                 120                 125

Met Pro Trp Phe Gln His Tyr Arg Asn Val Thr Val Gly Pro Pro Glu
        130                 135                 140

Asn Ile Glu Val Thr Pro Gly Glu Gly Ser Leu Ile Ile Arg Phe Ser
145                     150                 155                160

Ser Pro Phe Asp Ile Ala Asp Thr Ser Thr Ala Phe Phe Cys Tyr Tyr
                    165                 170                 175

Val His Tyr Trp Glu Lys Gly Gly Ile Gln Gln Val Lys Gly Pro Phe
                    180                 185                 190

Arg Ser Asn Ser Ile Ser Leu Asp Asn Leu Lys Pro Ser Arg Val Tyr
                    195                 200                 205

Cys Leu Gln Val Gln Ala Gln Leu Leu Trp Asn Lys Ser Asn Ile Phe
        210                 215                 220

Arg Val Gly His Leu Ser Asn Ile Ser Cys Tyr Glu Thr Met Ala Asp
225                     230                 235                240

Ala Ser Thr Glu Leu Gln Gln Val Ile Leu Ile Ser Val Gly Thr Phe
                    245                 250                 255

Ser Leu Leu Ser Val Leu Ala Gly Ala Cys Phe Phe Leu Val Leu Lys
        260                 265                 270

Tyr Arg Gly Leu Ile Lys Tyr Trp Phe His Thr Pro Pro Ser Ile Pro
        275                 280                 285

Leu Gln Ile Glu Glu Tyr Leu Lys Asp Pro Thr Gln Pro Ile Leu Glu
        290                 295                 300

Ala Leu Asp Lys Asp Ser Ser Pro Lys Asp Asp Val Trp Asp Ser Val
305                     310                 315                320

Ser Ile Ile Ser Phe Pro Glu Lys Glu Gln Glu Asp Val Leu Gln Thr
                    325                 330                 335

Leu
```

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: X is an amino acid with non-polar side chain
<220> FEATURE:
<221> NAME/KEY: X
<222> LOCATION: (3)..(3)
<223> OTHER INFORMATION: X is an amino acid with non-polar side chain
<220> FEATURE:

```
<221> NAME/KEY: X
<222> LOCATION: (5)..(6)
<223> OTHER INFORMATION: X is an amino acid with charged polar side
      chain

<400> SEQUENCE: 4

Xaa Pro Xaa Leu Xaa Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Val Pro Met Leu Lys Glu
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Val Pro Met Leu Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Pro Met Leu Lys Glu
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

Pro Met Leu Lys
1

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide

<400> SEQUENCE: 9

Val Pro Thr Leu Lys
1               5

<210> SEQ ID NO 10
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 10

Val Pro Ala Leu Arg
1               5

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

Asp Pro Thr Gln Pro Ile Leu Glu Ala Leu Asp Lys
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide

<400> SEQUENCE: 12

Asp Asp Val Trp Asp Ser Val Ser Ile Ile Ser Phe Pro Glu Lys
1               5                   10                  15

<210> SEQ ID NO 13
<211> LENGTH: 18
<212> TYPE: PRT
<213> ORGANISM: Artificial Sequence
<220> FEATURE:
<223> OTHER INFORMATION: Synthetic peptide

<400> SEQUENCE: 13

Tyr Trp Phe His Thr Pro Pro Ser Ile Pro Leu Gln Ile Glu Glu Tyr
1               5                   10                  15

Leu Lys
```

US 8,324,170 B2

INTERFERON GAMMA RECEPTOR BETA CHAIN COMPOSITIONS AND METHODS OF INHIBITING APOPTOSIS

RELATED APPLICATION

This application claims priority from U.S. Provisional Application No. 61/232,050, filed Aug. 7, 2009, the subject matter which is incorporated herein by reference.

GOVERNMENT FUNDING

This invention was made with government support under Grant Nos. PC0CA1037 and R01AG031903 awarded by The National Institutes of Health. The United States government has certain rights in the invention.

BACKGROUND

The process of programmed cell death or apoptosis has been shown to be centrally involved in the pathogenesis of the significant majority of human illnesses and injury states. The cellular attrition observed in most degenerative conditions is apoptotic in nature; conversely, a failure of apoptosis has been proposed to underlie many forms of cancer. The central role of apoptosis in human disease clearly brings with it clinical promise; for example, the strong possibility exists that attenuation of apoptotic death will significantly modulate the severity of degenerative disorders.

Abnormal regulation of apoptosis is a cause of several diseases, including cancer and neurodegenerative disorders among others. Bax is a 21-kDa member of the conserved Bcl-2 family of proteins involved in regulating programmed cell death. Bax plays a key role in the intrinsic pathway of apoptosis. Bcl-2 family proteins are characterized by the presence of four Bcl-2 homology (BH) domains. Antiapoptotic members (e.g., Bcl-2, Bcl-XL and Mcl-1) have all four BH domains (BH1-4). The proapoptotic members are further divided into multi-domain proteins (e.g., Bax, Bak and Bok) containing three BH domains (BH 1-3) or BH3-only proteins (e.g., Bim, Bid and PUMA, etc.,) containing just the BH-3 domain. The molecular mechanisms, by which these proteins function and interact is not fully understood, but their role in apoptosis is indisputable. Although it has been extensively studied how Bcl-2 family proteins influence each other, it is not well known how these proteins are regulated by non-Bcl-2 family proteins.

SUMMARY

The present invention relates to a method of inhibiting apoptosis in a cell. The method includes administering to the cell a therapeutically effective amount of cell penetrating peptide (CPP). The CPP consists of about 5 to about 41 amino acids and is substantially homologous to a portion of the C-terminal region of interferon gamma receptor 2 (IFNγR2). In some embodiments, the CPP comprises SEQ ID NO:1. In other embodiments the CPP comprises SEQ ID NO:2. In other embodiments the CPP consists essentially of SEQ ID NO:2. In still other embodiments the CPP comprises about 5 to about 10 amino acids and includes SEQ ID NO:2.

In one specific embodiment, a Ku70-derived Bax-inhibiting peptide selected from the group consisting of the VPMLKE (SEQ ID NO:5), VPMLK (SEQ ID NO:6), PMLKE (SEQ ID NO:7), PMLK (SEQ ID NO:8), VPTLK (SEQ ID NO:9), and VPALR (SEQ ID NO:10) can be administered.

In another embodiment, the Ku70-derived Bax-inhibiting peptide is of the following formula: $X^1PX^2LX^3X^4$ (SEQ ID NO: 4), wherein X1 is selected from amino acids with a non-polar side chain; $X^2$ is selected from amino acids with a non-polar side chain; $X^3$ is selected from amino acids with a charged polar side chain; $X^4$ is selected from amino acids with a charged polar side chain; and either $X^1$ or $X^4$ may be absent, although both may not be absent.

In some embodiments, the CPP binds to Bax in the cell and inhibits Bax mediated apoptosis in the cell. In some embodiments, the CPP inhibits Bax activation. In some embodiments, the CPP is capable of binding to inactive Bax and N-terminus exposed Bax molecules. The CPP apoptosis inhibiting activity can be independent of the Jak/Stat signal transduction pathway. The CPP can also suppress Bim dependent activation but not apoptosis induced by Bak expression in the cell.

The therapeutically effective amount can be an amount of CPP effective to inhibit apoptosis induced by Bax overexpression in the cell. In some embodiments, the Bax overexpression in the cell is induced by cytotoxic stresses elicited from chemo-and radiotherapy.

The present invention also relates to a cell penetrating peptide (CPP) for inhibiting apoptosis in a cell. The CPP consists of about 5 to about 10 amino acids and includes the amino acids of SEQ ID NO:2. In some aspects, the CPP includes SEQ ID NO:2. In other aspects, the CPP consists essentially of SEQ ID NO:2.

The present invention also relates to a pharmaceutical composition. The pharmaceutical composition includes a CPP. The CPP consists of about 5 to about 41 amino acids and is substantially homologous to a portion of the C-terminal region of IFNγR2. The composition also includes a Ku70-derived Bax-inhibiting peptide of the following formula: $X^1PX^2LX^3X^4$ (SEQ ID NO: 4), wherein $X^1$ is selected from amino acids with a non-polar side chain; $X^2$ is selected from amino acids with a non-polar side chain; $X^3$ is selected from amino acids with charged a polar side chain; $X^4$ is selected from amino acids with a charged polar side chain; and either $X^1$ or $X^4$ may be absent, although both may not be absent. The pharmaceutical composition further includes a pharmaceutical carrier.

In an aspect of the invention, the pharmaceutical composition includes a CPP that comprises SEQ ID NO:2. The pharmaceutical composition also includes a Ku70-derived Bax-inhibiting peptide selected from the group consisting of VPMLKE (SEQ ID NO:5), VPMLK (SEQ ID NO:6), PMLKE (SEQ ID NO:7), PMLK (SEQ ID NO:8), VPTLK (SEQ ID NO:9), and VPALR (SEQ ID NO:10) and a pharmaceutical carrier.

The present invention also includes a method of treating an apoptotic disease in a subject. The method includes administering to the subject a therapeutically effective amount of CPP, wherein the CPP consists of about 5 to about 41 amino acids and is substantially homologous to a portion of the C-terminal region of IFNγR2. In some embodiments, the CPP comprises about 5 to about 10 amino acids and includes SEQ ID NO:2. In some embodiments, the CPP includes SEQ ID NO:2. In other embodiments, the CPP consists essentially of SEQ ID NO:2. In some embodiments, the method further includes administering a Ku70-derived Bax-inhibiting peptide selected from the group consisting of VPMLKE (SEQ ID NO:5), VPMLK (SEQ ID NO:6), PMLKE (SEQ ID NO:7), PMLK (SEQ ID NO:8), VPTLK (SEQ ID NO:9), and VPALR (SEQ ID NO:10).

The therapeutically effective amount of CPP can include an amount effective to inhibit apoptosis induced by Bax overexpression in one or more cells in the subject. In some embodiments, the apoptotic disease includes at least one of ischemic disease, stroke, myocardial infarction, degenerative disease, and an infectious agent. In some embodiments, the apoptotic disease is induced by the administration of one or more anticancer drug(s) or UV/X-ray irradiation to the subject.

The present invention also relates to a method of treating a proliferative disorder in a subject. The method includes administering to the subject a therapeutically effective amount of an anti-proliferative agent and a therapeutically effective amount of a CPP, wherein the CPP consists of about 5 to about 41 amino acids and is substantially homologous to a portion of the C-terminal region of IFNγR2. In some embodiments, the CPP comprises about 5 to about 10 amino acids and includes SEQ ID NO:2. In some embodiments, the CPP includes SEQ ID NO:2. In other embodiments the CPP consists essentially of SEQ ID NO:2.

The proliferative disorder can include cancer and the anti-proliferative agent can be administered at an amount effective to treat the cancer. In some embodiments, the therapeutically effective amount of CPP is an amount effective to mitigate chemotherapy induced apoptosis of megakaryocytes of the subject without substantially inhibiting platelet formation of the megakaryocytes.

In certain embodiments the method further includes administering a Ku70-derived Bax-inhibiting peptide selected from the group consisting of VPMLKE (SEQ ID NO:5), VPMLK (SEQ ID NO:6), PMLKE (SEQ ID NO:7), PMLK (SEQ ID NO:8), VPTLK (SEQ ID NO:9), and VPALR (SEQ ID NO:10).

The present invention further relates to a method of preserving cells and organs for transfusions or transplantation. The method includes storing the cells or organs in a therapeutically effective amount of CPP, wherein the CPP consists of about 5 to about 41 amino acids and is substantially homologous to a portion of the C-terminal region of IFNγR2. In some embodiments the CPP comprises about 5 to about 10 amino acids and includes SEQ ID NO:2. In some embodiments, the CPP includes SEQ ID NO:2. In other embodiments, the CPP consists essentially of SEQ ID NO:2.

In certain embodiments, the method further includes storing the cells in a Ku70-derived Bax-inhibiting peptide selected from the group consisting of VPMLKE (SEQ ID NO:5), VPMLK (SEQ ID NO:6), PMLKE (SEQ ID NO:7), PMLK (SEQ ID NO:8), VPTLK (SEQ ID NO:9), and VPALR (SEQ ID NO:10).

BRIEF DESCRIPTION OF DRAWINGS

FIG. 1 (A-B) illustrates that IFNγR2 cytoplasmic domain inhibits Bax-induced cell death. (A) The C-terminus (amino acids 263-337) of interferon gamma receptor beta chain (IFNγR2) was cloned as a Bax suppressor in a yeast-based functional screen for Bax inhibitors. The image shows rescue of yeast growth from Bax expression by IFNγR2 (amino acids 263-337) and Ku70 (served as a positive control). (B) Schematic representation of IFNγR2 wild-type (w.t.) protein and its truncated forms used in this study.

FIG. 2 (A-E) illustrates that IFNγR2 protects cells from Bax-induced cell death independent of the Jak2-signaling pathway. (A) The IFNγR2 C-terminal region (296-337) inhibited apoptosis induced by Bax overexpression. HEK293 cells were transiently co-transfected with pcDNA3-h Bax and pEGFP C2-IFNγR2 wild type, -IFNγR2$_{1-295}$ or -IFNγR2$_{296-337}$, and apoptosis was determined 24 h after the transfection, as described in the Materials and Methods section. Each bar represents the mean of triplicate samples and standard errors, and statistical significance was determined by an unpaired student t test: ***p <0.001. (B) Plasmid-mediated expression of IFNγR2 inhibited etoposide-induced apoptosis in IFNγR2 null cells. IFNγR2 null cells were transiently transfected (see Materials and Methods) with pEGFP-C2-IFNγR2wild type, -IFNγR2$_{1-295}$ or-IFNγR2$_{296-337}$. One day after the transfection, cells were treated with 10 μM etoposide for 24 h, and apoptosis was detected by using Hoechst nuclear staining. Each bar represents the mean of triplicate samples and standard errors, and statistical significance was determined by an unpaired student t test: *p <0.05, and *p <0.001. (C) Plasmid-mediated expression of IFNγR2 inhibited etoposide-induced Caspase 3 activation in IFNγR2 null cells. IFNγR2 null cells were transiently transfected (see Materials and Methods) with pEGFP-C2-IFNγR2wild type, -IFNγR2$_{1-295}$ or -IFNγR2$_{296-337}$. One day after transfection, the cells were treated with 10 μM etoposide for 24 h. Caspase 3activity was measured as described in the Materials and Methods section. Each bar represents the mean of triplicate samples and standard errors, and statistical significance was determined by an unpaired student t test: *p <0.001.(D and E) Bax inhibition by IFNγR2 is independent of Jak2. (D) Jak2 null cells were transiently transfected with pEGFP-C2-IFNγR2wild type, -IFNγR2$_{1-295}$ or -IFNγR2$_{296-337}$. One day after the transfection, the cells were treated with 10 μM etoposide for 24 h. Apoptosis was detected by using Hoechst nuclear staining as described in the Materials and Methods section. Each bar represents the mean of triplicate samples and standard errors, and statistical significance was determined by an unpaired student t test: *p <0.001. (E) Jak2 null cells were transiently transfected with pEGFP-C2-IFNγR2wild type, -IFNγR2$_{1-295}$ or -IFNγR2$_{296-337}$. One day after transfection the cells were treated with etoposide 10 μM for 24 h. Caspase 3 activity was measured as described in the Materials and Methods section. Each bar represents the mean of triplicate samples and standard errors, and statistical significance was determined by an unpaired student t test: *p <0.001.

FIG. 3 (A-B) illustrates that IFNγR2 knock-down sensitizes HeLa cells to apoptosis. (A) IFNγR2 shRNA was expressed in HeLa cells from a lentivirus vector. For control shRNA, non-IFNγR2-targeted shRNA (targeting GFP), and empty vector were used. IFNγR2 expression levels were analyzed by western blotting using IFNγR2 C-20 antibody (Santa Cruz). Actin was used for a loading control. (B) HeLa cells expressing shRNA against IFNγR2 were treated with 10 μM etoposide for 24 h. Apoptosis was detected by Hoechst dye nuclear staining as described in the Materials and Methods section. Each bar represents the mean of triplicate samples and standard errors, and statistical significance was determined by an unpaired student t test: ***p <0.001.

FIG. 4 (A-B) illustrates that IFNγR2 C-terminus inhibits Bim-induced apoptosis but not Bak-induced apoptosis. (A) IFNγR2 inhibited Bim-induced apoptosis in HEK293T cells. HEK293T cells were transiently co-transfected with pcDNA3-h Bim EL and pEGFP-C2-IFNγR2wild type, -IFNγR2$_{1-295}$ or IFNγR2$_{296-337}$ as described in Materials and Methods. Apoptosis induction was analyzed 24 h after the transfection by using Hoechst dye nuclear staining. Each bar represents the mean of triplicate samples and standard errors, and statistical significance was determined by an unpaired student t test: ***p <0.001. (B) IFNγR2 did not inhibit Bak-induced apoptosis. HEK293 cells were transiently co-transfected (see Materials and Methods) with pcDNA3-h Bak and pEGFP-C2-IFNγR2wild type, -IFNγR2$_{1-295}$ or-IFNγ

R2$_{296-337}$, and apoptosis induction was analyzed 24 h after the transfection. Each bar represents the mean of triplicate samples and standard errors.

FIG. 5 (A-K) illustrates that localization of IFNγR2. HeLa and HEK293 cells were transfected with pEGFP-C2 IFNγR2wild type, pEGFP-C2-IFNγR2$_{1-295}$ or pEGFP-C2-IFNγR2$_{296-337}$. One day after the transfection, the subcellular locations of the IFNγR2-EGFP fusion proteins were determined by fluorescence microscopy. (A and B) HeLa cells transfected with pEGFP vector. (C and D) HeLa cells transfected with pEGFP-C2-IFNγR2wild type. (E and F) HeLa cells transfected with pEGFP-C2-IFNγR2$_{296-337}$. (G and H) HeLa cells transfected with pEGFP-C2-IFNγR21-295. (I) HEK293 cells transfected with pEGFP-C2-IFNγR2wild type. (J) Mito-tracker staining of HE293 cells transfected with pEGFP-C2-IFNγR2wild type as in (I). Images are 40×magnification. (K) The percentages of cells showing a punctate pattern of GFP signals (mitochondrion-like distribution) in each group are presented in K. Each bar represents the mean of triplicate samples and standard errors.

FIG. 6 (A-D) illustrates a Western blot analysis of EGFP-tagged IFNγR2proteins (A) Expression of IFNγR2 EGFP fusion proteins in IFNγR2 null (mutant HT1080) cells after the transient transfection. Cells were transfected with pEGFP-C2-IFNγR2wild type, pEGFP-C2-IFNγR2$_{1-295}$ or pEGFP C2-IFNγR2$_{296-337}$. One day after the transfection, the cells were collected for western blot analysis with anti-EGFP polyclonal antibody (Abcam). IFNγR2-GFP fusion proteins were detected as bands with the expected molecular weights. However, smaller forms, probably resulting from protease-dependent cleavage, were also detected (* indicates a cleaved form of IFNγR2-GFP fusion proteins). (B) Western blot analysis of IFNγR2-GFP fusion proteins in HEK293 cells. Cells were transfected with pEGFP-C2-IFNγR2wild type, pEGFP-C2-IFNγR2$_{1-295}$ or pEGFP-C2-IFNγR2$_{296-337}$. One day after the transfection, cells were collected for western blot analysis using EGFP polyclonal antibody (Abcam). Although intact (non-cleaved) GFP-IFNγR2$_{296-337}$ was detected, intact IFNγR2wild type-GFP and IFNγR2$_{1-295}$-GFP were not detected. Instead, cleaved forms of these proteins were observed (* indicates these cleaved forms). (C and D) Confirmation of expression of IFNγR2-GFP fusion proteins by enrichment of the fusion proteins using immunoprecipitation. One day after the transfection of pEGFP-C2-IFNγR2wild type (C), pEGFP-C2-IFNγR2$_{1-295}$ (C), or pEGFP-C2-IFNγR2$_{296-337}$ (D), HEK293 cells were collected and immunoprecipitation was performed by using anti-GFP polyclonal antibody (Abcam). The samples were subjected to western blot analysis using anti IFNγR2 detecting the N-terminal portion of IFNγR2 as an epitope (IFNγR2 antibody from Fitzgerald) (C) or anti-IFNγR2 detecting the C-terminal 20 amino acids of IFNγR2 (IFNγR2 C20 antibody from Santa Cruz) (D). Intact fusion proteins were detected as bands with the expected molecular weights (approximately 67 kDa in (C) and 34 kDa in (D)). In the "Input"lanes of (C), the strong background staining prevented the detection of both endogenous IFNγR2 and INFγR2-GFP fusion proteins. In the "Input" lanes of (D), endogenous IFNγR2 as well as fusion protein were detected by anti-IFNγR2antibody. Seven hundred micrograms of total protein were used in the IP experiments, and 150 pg of total protein was used for input level.

FIG. 7 (A-E) illustrates that the C-terminal portion of IFNγR2 (amino acids 296-337) is sufficient to inhibit Bax activation. HeLa cells were transfected with pEGFP-C2 vector (A), pEGFP-C2-IFNγR2$_{1-295}$ (B), -IFNγR2$_{296-337}$ (C) or -IFNγR2wild type (D) as described in Materials and Methods. After 24 h of transfection, the cells were treated with staurosporine 100 nM for 3 h. Then, the cells were washed with phosphate buffer pH 7.4 (PBS), fixed by paraformaldehyde 1%, permeabilized with Triton X-100 (0.02%), blocked with goat serum, and the activation of Bax was analyzed by immunostaining with anti-Bax 6A7 monoclonal antibody (which recognizes active Bax). Arrowheads indicate cells both positive for GFP and active Bax (Bax 6A7+cells). Images are at 20×magnification. (E) Percentages of cells that were stained by Bax 6A7 Ab among GFP positive cells are shown. Each bar represents the mean of triplicate samples and standard errors, and statistical significance was determined by an unpaired student t test: ***p <0.001.

FIG. 8 (A-E) illustrates that IFNγR2 interacts with Bax. (A and B) Co-immunoprecipitation of endogenous IFNγR2 and Bax. HEK293T cells were lysed using CHAPS or NP40 buffer as described in Materials and Methods. Immunoprecipitation (IP) was performed in the same buffer (NP40 or CHAPS) with an anti-Bax polyclonal (A) or an anti-IFNγR2 mouse monoclonal antibody (B). (A) HEK293T cell lysates were prepared in CHAPS or NP40 buffer. IP and western blot (WB) were performed with anti-Bax polyclonal (BD Pharmingen) and anti-IFNγR2 monoclonal (Fitzgerald) antibodies, respectively. (B) HEK293T cells were lysed with NP40 buffer, IP and WB were performed with anti-IFNγR2 monoclonal (Fitzgerald) and anti-Bax polyclonal (N20), respectively. (C) Examination of the interaction of purified recombinant Bax and IFNγR2 proteins. Protein G sepharose beads were pre-incubated with pre-immune mouse IgG (IgG) or anti-Bax monoclonal antibody B9 (Anti-Bax (B9)). Then, recombinant proteins of human Bax ΔTM (Bax C-terminal transmembrane truncated human Bax) and IFNγR2$_{263-337}$ tagged with thioredoxin (rTrx) were incubated with these beads as described in Materials and Methods. After extensive washing of the beads with buffer, beads were boiled in Laemmli buffer. Samples were analyzed by western blot using anti-IFNγR2 antibody (C20, Santa Cruz) and anti-Bax antibody (N20, Santa Cruz). (D) Bcl-2 competed with IFNγR2 to bind Bax. HEK 293T cells were lysed using NP40 buffer. Co-immunoprecipitation was performed with anti-Bax polyclonal antibody (BD Biosciences) in the presence of exogenously added recombinant Bcl-2 (final concentration is indicated in the figure). Western blot analysis of immunoprecipitated samples was performed by using anti-Bcl-2 monoclonal antibody (Santa Cruz) or anti-IFNγR2 monoclonal antibody (Fitzgerald), or anti-Bax monoclonal antibody (B9, Santa Cruz). (E) Bax inhibiting peptide (BIP) derived from Ku70 (VPTLK) did not compete with IFNγR2 to bind Bax. HEK 293T cells were lysed in CHAPS buffer, and BIP was added to the cell lysate to examine its effect on the interaction of Bax and IFNγR2 as described in Materials and Methods. Co-immunoprecipitation was performed with anti-IFNγR2 monoclonal antibody (Fitzgerald), and western blotting was done using anti-Bax N20 polyclonal antibody (Santa Cruz).

FIG. 9 (A-C) illustrates the detection of the C-terminal fragment of IFNγR2 in transformed cells. (A) western blot analysis of IFNγR2 in DAMI (human megakaryoblast cell line), HEK293T (SV40 Large T-transformed cell line), and HUVEC (non-transformed cells). Total cell lysates (150 μg protein/lane) were analyzed. INFγR2 null cells were used as a negative control sample to distinguish specific bands from nonspecific bands (A, right lane). (B) Enrichment of the C terminal fragment by immunoprecipitation (IP). Cells (HUVEC, DAMI and HEK293T cells) were lysed using RIPA buffer. Both IP and WB were performed with anti-IFNγR2 (C20 Santa Cruz) polyclonal antibody. The C-terminal fragment of IFNγR2 was detected in DAMI and HEK293T cells, but not in HUVEC. (C) Western blot analysis of IFNγR2 in various human cell types: human normal mammary epithelial cell line (4A100), non-tumorigenic immortalized breast cell line (HME1), tumorigenic human breast cancer cell line (MDAMD 468), non-tumorigenic (RWPE1) and tumorigenic (RWPE2) human prostate cell lines, and tumorigenic prostate cancer cell lines (LNCap and PC3). INFγR2 null cells were used as a negative control to distinguish specific bands from non-specific bands detected with the IFNγR2 C20 antibody.

FIG. 10 (A-B) illustrates the measurement of cellular concentrations of IFNγR2 and Bax. Purified recombinant proteins of rTrx-IFNγR2$_{263-337}$ and Bax (ΔTM) were used as standards. DAMI cells were lysed in hypotonic buffer supplemented with protease inhibitors. Each subcellular fraction from equivalent cell numbers, and sequential dilutions of protein standards were subjected to SDS-PAGE, and transferred to nitrocellulose membrane. Bax-N20-HRP antibody (Santa Cruz) and IFNγR2 C-20 antibody (Santa Cruz) were used to detect Bax (A) and IFNγR2 (B), respectively. Signal intensities were analyzed by using BioRad Gel Doc and Quantity One 4.5.1 software from BioRad. LDH, F1 αand YY1 were used as cytosolic, mitochondrial and nuclear markers, respectively.

DETAILED DESCRIPTION

The present invention generally relates to a method of inhibiting or mitigating apoptosis in a cell and particularly relates to method of inhibiting or mitigating apoptosis in cells of tissue using a Bax inhibitor. It was found that the cytoplasmic domain (or C-terminal domain) of the interferon gamma receptor beta chain (IFNγR2) acts as a novel Bax suppressor in mammalian cells. Bax is a well-known pro-apoptotic protein that mediates intrinsic cell-death signaling. The C-terminal domain of IFNγR2 can be used to design cell penetrating peptides (CPPs) that can inhibit the activation of Bax in human cell lines, thereby inhibiting Bax mediated apoptosis of the cells. CPPs in accordance with one aspect of the present invention that can inhibit activation of Bax in human cells can have an amino acid sequence substantially homologous to a portion of the C-terminal region 5 to 41 amino acid sequence (SEQ ID NO:1) of the C-terminus of IFNγR2 (IFNγ R2$_{296-337}$).

CPPs derived from or based on the amino acid sequence of the C-terminus of IFNγR2 do not contain the Jak2-binding domain; and therefore, the anti-apoptotic function of IFNγR2 is independent of JAK/STAT signaling. CPPs derived from or based on the C-terminus of IFNγR2 can also rescue human cells from apoptosis induced by overexpression of Bax but not Bak. By way of example, CPPs derived from or based on the amino acid sequence of the C-terminus of IFNγR2 can rescue Bim induced apoptosis (Bax mediated) (FIG. 4A), but not rescue cells from apoptosis induced by Bak mediated apoptosis (FIG. 4B).

CPPs derived from or based on the amino acid sequence of the C-terminus of IFNγR2 can bind to both inactive Bax and active N-terminus exposed Bax molecules. Bax activation involves exposure of the protein's N-terminus by a conformational change followed by Bax translocation from the cytosol to mitochondria (Li et al., Cell Death Differ 2007, Nechushtan et al., EMBO J, 1999; 18:2330-41; Wolter et al., J Cell Biol 139:1281-92, 1997). The Example below shows that IFNγR2 is able to bind to the active exposed N-terminus Bax molecules and inhibits the conformational change and mitochondrial translocation of Bax (FIG. 7). The Example below further illustrates that IFNγR2 interacts with Bax in a detergent-free buffer (CHAPS) that maintains the inactive conformation of Bax (FIG. 8), indicating that the inventive CPPs bind to and inhibit inactive Bax.

One aspect of the present invention therefore relates to a method of inhibiting apoptosis in a cell by administering to the cell a therapeutically effective amount of cell penetrating peptide (CPP). The CPP can consist of about 5 to about 41 amino acids and be substantially homologous to a portion of the amino acid sequence of the C-terminal region of interferon gamma receptor 2 (IFNγR2). An "effective amount" or "therapeutically effective amount" of CPP administered to a cell is the amount of the CPP effective to mitigate Bax mediated apoptosis in the cell. In some embodiments, the Bax mediated apoptosis is induced by cytotoxic stresses elicited from chemo-and radiotherapy delivered to the cell.

In one embodiment of the invention, the CPP can have an amino acid sequence substantially homologous to the amino acid sequence of SEQ ID NO: 1. By "substantially homologous" to the amino acid sequence of SEQ ID NO: 1 it is meant that the CPP can be a a fragment, analog or derivative of mammalian SEQ ID NO: 1 that differs from the amino acid sequence of SEQ ID NO: 1 in one or more amino acids. The amino sequence of such CPPs can feature a deletion, addition, or substitution of one or more amino acids of SEQ ID NO: 1. Amino acid insertions are preferably of about 1 to 4 contiguous amino acids, and deletions are preferably of about 1 to 10 contiguous amino acids. CPP fragments substantially homologous to the amino acid sequence of SEQ ID NO: 1 can substantially maintain the CPPs functional activity of inhibiting Bax mediated apoptosis in cells. In one example, a CPP having an amino acid sequence substantially homologous to SEQ ID NO:1 can have an amino acid sequence that is at least about 90%, about 91%, about 92%, about 93%, about 94%, about 95%, about 96%, about 97%, about 98%, or about 99% homologous to the amino acid sequence of SEQ ID NO: 1.

CPP Bax inhibiting fragments of the amino acid sequence of SEQ ID NO: 1 can be obtained by screening peptides recombinantly produced or chemically synthesized and tested for Bax inhibiting activity. For example, a CPP fragment of a peptide having an amino acid sequence of SEQ ID NO: 1 may be arbitrarily divided into fragments of desired length with no overlap of the fragments, or preferably divided into overlapping fragments of a desired length. The fragments can be produced and tested to identify those peptidyl fragments, which can function as Bax inhibiting peptides.

In some embodiments, the CPP can be a peptide of about 5 to about 10 amino acids in length and include each of the individual amino acids of SEQ ID NO:2 (PILEA). It is further contemplated that each of the individual amino acids of SEQ ID NO:2 can be included in such a peptide at any position relative to each other. In one particular embodiment of the invention, a five amino acid peptide corresponding to SEQ ID NO:2, has cell penetration activity and upon administration to the cell is sufficient to inhibit Bax mediated apoptosis.

The five amino acid peptide of SEQ ID NO:2, as well as variants and modified peptides (e.g., modified for better membrane permeablization or longer stability) are also cell penetrating peptides, and may be used to protect cells from apoptosis in accordance with the present invention. For example, CPPs of the present invention may further include peptides with slight modifications (e.g., substitution of similar charged amino acids or addition of 1, 2 or 3 innocuous amino acids at either end or by the addition of an innocuous entity or moiety) to the peptide sequences described herein. By "innocuous", it is meant that the amino acid(s) or entities do not substantially reduce the Bax-inhibiting activity of the core peptide sequence PILEA (SEQ ID NO: 2). Therefore, in some embodiments, a composition comprising a Bax-inhibiting peptide of the present invention includes a peptide described herein (e.g., PILEA (SEQ ID NO: 2)), with additions of 1, 2 or 3 innocuous amino acids at either end and/or innocuous amino acid substitutions. The present invention can also include peptides in which sequences described above are repeated multiple times.

However, peptide delivery and therapeutic administration may be limited by permeability and selectivity problems involving the cell membrane (Morris et al., Nat. Biotechnology. 19(12):1173-1176, 2001). Therefore, in some embodiments CPPs can further include the addition of small protein domains called protein transduction domains (PTD's) to either end of the peptide. PTD's can aid in either the transport of CPPs to specific target cells or to aid the stability of the molecule as they have been shown to cross biological membranes and act independently from transporters or specific receptors to promote delivery of peptides into cells (see Hawiger, Curr. Opin. Chem. Biol. 3(1):88-94, 1999).

A CPP of the present invention may be administered to a cell in any manner known in the art, which allows for the delivery of the CPP inside the cell. In some embodiments, there is no need to use a delivery tool, such as a liposome to administer a CPP to a cell given the cell penetrating property of the peptide. One example of a method of administering a CPP to a cell is to add an effective amount of CPP directly into culture media to protect cells from cytotoxic stresses.

In some embodiments of the invention, an additional membrane permeable peptide, which inhibits Bax-mediated apoptosis, may be co-administered to a cell with the inventive CPPs described above. In some particular embodiments, the co-administered peptide includes Ku-70 derived Bax-inhibiting peptides (BIPs). These BIPs are described in U.S. Pat. No. 7,314,866 B2, which is incorporated herein by reference.

A BIP for use in the present invention can include VPMLKE (SEQ ID NO: 5), VPMLK (SEQ ID NO: 6), PMLKE (SEQ ID NO: 7), PMLK (SEQ ID NO: 8), VPTLK (SEQ ID NO: 9), or VPALR (SEQ ID NO: 10). Advantageously VPMLK (SEQ ID NO:6), PMLKE (SEQ ID NO:7), PMLK (SEQ ID NO:8), VPTLK (SEQ ID NO:9), and VPALR (SEQ ID NO:10) are also cell membrane permeable and do not require a cell delivery system, such as liposomes.

In another particular embodiment, a BIP for use in the methods of the present invention includes a peptide of the general formula $X^1PX^2LX^3X^4$ (SEQ ID NO:4), wherein:

$X^1$=Amino acids with a non-polar side chain, such as Glycine (G), Alanine (A), Valine (V), Leucine (L), Isoleucine (I), Methionine (M), Proline (P), Phenylalanine (F), or Tryptophan (W).

$X^2$=Amino acids with a non-polar side chain, such as Glycine (G), Alanine (A), Valine (V), Leucine (L), Isoleucine (I), Methionine (M), Proline (P), Phenylalanine (F), Tryptophan (W) or Threonine (T).

$X^3$=Amino acids with a charged polar side chain, such as Lysine (K), Arginine (R), Histidine (H), Aspartic acid (D), Glutamic acid (E), and $X^4$=Amino acids with a charged polar side chain, such as Lysine (K), Arginine (R), Histidine (H), Aspartic acid (D), Glutamic acid (E).

Either $X^1$ or $X^4$ may be absent.

The present invention also relates to a pharmaceutical composition comprising a CPP as described above. A pharmaceutical composition in accordance with invention can further include a BIP as described above and/or a suitable pharmaceutical carrier. In one exemplary embodiment, the pharmaceutical composition includes a five amino acid long peptide of SEQ ID NO:2, a BIP selected from the group consisting of the VPMLKE (SEQ ID NO:5), VPMLK (SEQ ID NO:6), PMLKE (SEQ ID NO:7), PMLK (SEQ ID NO:8), VPTLK (SEQ ID NO:9), and VPALR (SEQ ID NO:10), and a pharmaceutical carrier.

In another exemplary embodiment, the pharmaceutical composition includes a five amino acid long peptide of SEQ ID NO:2, a BIP having the following formula: $X^1PX^2LX^3X^4$ (SEQ ID NO: 4), wherein $X^1$ is selected from amino acids with a non-polar side chain; $X^2$ is selected from amino acids with a non-polar side chain; $X^3$ is selected from amino acids with a charged polar side chain; $X^4$ is selected from amino acids with a charged polar side chain; and either $X^1$ or $X^4$ may be absent, although both may not be absent, and a pharmaceutical carrier.

The pharmaceutical compositions of the present invention can be administered to a subject by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively or concurrently, administration can be by the oral route. The dosage administered will be dependent upon the age, health, and weight of the patient, kind of concurrent treatment, if any, frequency of treatment, and the nature of the effect desired.

The pharmaceutical compositions of the present invention can include pharmaceutically acceptable carriers comprising excipients and auxiliaries that facilitate processing of the active agents into preparations that can be used pharmaceutically. The pharmaceutical preparations of the present invention are manufactured in a manner that is, itself, known, for example, by means of conventional mixing, granulating, dragee-making, dissolving, or lyophilizing processes.

Formulations for parenteral administration include aqueous solutions of the active compounds in water-soluble form, for example, water-soluble salts and alkaline solutions. Especially preferred salts are maleate, fumarate, succinate, S,S tartrate, or R,R tartrate. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

It is well known that apoptosis, and particularly Bax mediated apoptosis, is centrally involved in the pathogenesis of many human illnesses and injury states. The following references describe the Bax protein playing a key role in various diseases: Injury-induced neuron death-Deckwerth, et al. Neuron. 17:401-411, 1996; Martin, et al., J. Compo Neurol. 433: 299-311, 2001; Kirkland, et al., J. Neurosci. 22:6480-90, 2002; Alzheimer disease-MacGibbon, et al., Brain Res. 750: 223-234, 1997; Selznick, et al., J. Neuropathol. Exp. Neurol. 59:271-279, 2000; Cao, et al., J. Cereb. Blood Flow Metab. 21:321-333, 2001; Zhang, et al., J. Cell Biol. 156:519-529, 2002; Ischemia induced cell damage-Kaneda, et al., Brain Res. 815: 11-20, 1999; Gibson, et al., Mol. Med. 7:644-655, 2001; HIV (AIDS) and Bax: Castedo, et al., J. Exp. Med. 45 194:1097-1110, 2001; Drug-induced neuron death-Dargusch, et al., J. Neurochem. 76:295-301, 2001; Parkinson's disease-Ploix and Spier, Trends Neurosci. 24:255, 2001; Huntington's disease-Antonawich, et al., Brain Res. Bull. 57:647-649, 2002.

Therefore, in another embodiment, a pharmaceutical composition of the present invention can be administered to a subject for the treatment of an apoptotic disease. The method includes administering a therapeutically effective amount of a pharmaceutical composition comprising CPP to the subject. The term "therapeutically effective amount" refers to the amount of an inventive pharmaceutical composition required to reduce the severity and/or frequency of symptoms, elimination of symptoms and/or underlying cause, prevention of the occurrence of symptoms and/or their underlying cause, and improvement or remediation of disease. For example, a therapeutically effective amount of a pharmaceutical composition of the present invention encompasses the reduction of Bax mediated cell or tissue death in a subject.

Apoptotic diseases and related disorders as contemplated by the present invention, can include stroke, heart attack, ischemia, degenerative diseases (neuron and muscle, e.g., Alzheimer disease, Parkinson's disease, cardiomyocyte degeneration, etc), macular degeneration, hypoxia induced apoptosis, ischemia reperfusion injury, atrophy, infection by parasitic organisms (virus, bacteria, yeast, or protozoa, etc), side effects of other drugs (e.g., anti-cancer drugs), UV/X-ray irradiation, and several other pathological conditions triggering cell death signals.

As described above, the compositions described herein can be used to inhibit Bax mediated cell death wherein Bax overexpression in the cell is induced by chemo-and radiotherapy. In one exemplary embodiment, a pharmaceutical composition described above in accordance with the present invention can protect megakaryocytes from chemotherapy induced apoptosis without substantially affecting the ability of megakaryocytes to produce and release platelets.

It is further contemplated that the pharmaceutical compositions in accordance with the invention can be used in a combination therapy or adjunctive therapy with antiproliferative agents or chemotherapeutic agents for the treatment of proliferative disorders, such as neoplastic disorders or cancer. The phrase "combination therapy" embraces the administration of the pharmaceutical compositions including CPPs and a therapeutic agent as part of a specific treatment regimen intended to provide a beneficial effect from the co-action of these therapeutic agents.

Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The apoptotic disease treated by the combination therapy can include proliferative diseases, such as neoplastic disorders (e.g., leukemia) and cancer. Besides being useful for human treatment, the combination therapy is also useful for veterinary treatment of companion animals, exotic and farm animals, including rodents, horses, dogs, and cats.

In another embodiment of the invention, the therapeutic agents administered in combination therapy with the inventive CPP pharmaceutical compositions can comprise at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chmotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agents available in commercial use, in clinical evaluation and in pre-clinical development, which could be included in the present invention by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

The CPPs in accordance with the present invention allow the combination therapeutic agents and therapies of the present invention to be administered at a higher dose, that is, at a dose higher than has been conventionally used in clinical situations because of the risk of thrombocytopenia.

The present invention also provides a method of preserving tissues and organs for transfusions or transplantation. According to the present invention, the cells, tissue, or organ can be stored in and/or contacted with a composition including an effective amount of CPP. The effective amount of CPP is an amount effective to mitigate Bax mediated apoptosis of the cells, tissue, or organ of interest. In some embodiments, a composition for storing cells or organs can include an effective amount of CPP and an organ preservation solution. In some embodiments, the composition can further comprise a Ku70-derived BIP peptide.

Typically, the tissue or organ has been separated from its usual nutrient sources, e.g., the blood circulation of a living animal or person. Organ preservation solutions depend on contacting, storing and/or perfusing the organ with a supportive preservation solution designed to provide pH buffering, osmotic balance and/or some minimal nutritional support, e.g., in the form of glucose and a limited set of other basic nutrients. This approach is typically combined with reduction in organ temperature to just above the freezing point of water. This is intended to reduce the metabolic rate of organ tissues, thus slowing the consumption of nutrients and the production of waste products. Thus, in some embodiments, the CPP containing compositions of the present invention can be employed at the hypothermic ranges commonly used in the art, which can range from below 20° C. to about 4° C. These art-known preservative solutions include, for example, isotonic saline solutions, that may contain, in various proportions, salts, sugars, osmotic agents, local anesthetic, buffers, and other such agents, as described, simply by way of example, by Berdyaev et al., U.S. Pat. No. 5,432,053; Belzer et al., described by U.S. Pat. Nos. 4,798,824, 4,879,283; and 4,873,230; Taylor, U.S. Pat. No. 5,405,742; Dohi et al., U.S. Pat. No. 5,565,317; Stern et al., U.S. Pat. Nos. 5,370,989 and 5,552,267.

The term, "organ" as used herein encompasses both solid organs, e.g., kidney, heart, liver, lung, pancreas, as well as functional parts of organs, e.g., segments of skin, sections of artery, transplantable lobes of a liver, kidney, lung, and other organs. The term, "tissue" refers herein to viable cellular materials in an aggregate form, e.g., small portions of an organ, as well as dispersed cells, e.g., cells dispersed, isolated and/or grown from heart muscle, liver or kidney, including bone marrow cells and progeny cells, blood born stem cells and progeny, and the various other art-known blood elements, unless otherwise specified.

The invention also contemplates using a CPP containing composition for localized or systemic circulatory or perfusion support for organs or tissues acutely deprived of normal blood circulation caused by trauma, e.g., infusions or temporary circulation of the inventive compositions to support a partially severed limb, or analogous conditions, until surgical repair of damaged vasculature is achieved.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE

We show in the following example that interferon gamma receptor beta chain (IFNγR2) is a Bax inhibitor not belonging to the Bcl-2 family of proteins.

IFNγR2 is part of the interferon γ (IFN γ) receptor complex composed of IFNγR alpha chain (IFNγR1) and IFNγR2. IFNγR2 interacts with Jak2 prior to IFNγ binding. Upon IFNγ binding, a conformational change in the receptor complex occurs, followed by auto-phosphorylation of Jak kinase, phosphorylation of IFNγR1, and recruitment of STAT1, leading to STAT1 activation. IFNγR2 is expressed in the plasma membrane, endoplasmic reticulum (ER) and mitochondria. At present, the biological significance of the mitochondrial localization of IFNγR2 is not known. IFNγR2 knock-out mice show no sensitivity to IFNγ and are unable to prevent infection by Lsteria monocytogenes. Previous studies showed that IFNγR2 plays a role in apoptosis regulation as a signal-transduction molecule of IFNγ (reviewed in ref. 19), but to our knowledge, there is no report describing the apoptosis regulating activity of IFNγR2 itself.

Here we report that the C-terminus of IFNγR2 has a Bax-inhibiting activity that is independent of the Jak/STAT signal transduction pathway. We also found that certain cancer cell lines (DAMI cells, MDA-MD468 cells and PC3) express a truncated form of IFNγR2 containing the C-terminal Bax-inhibitory domain. The presence of this C-terminal fragment of IFNγR2 in the cytosol may help such cancer cells increase their resistance to cytotoxic stresses, including those elicited by chemo-and radiotherapy.

Yeast-Based Functional Screening for Bax Inhibitors

The yeast strain EGY48 was used for the yeast functional screening for Bax inhibitors. Mouse Bax was expressed under a galactose-inducible promoter using pGilda vector as reported. Yeast expression libraries of cDNAs of mouse brain and a human cell line (HeLa) were prepared in pYES2 and pJG4-5 vectors, respectively.

Cell Culture and Transfection Cell Culture

HT1080 (wild type, IFNγR2 null mutant and JAK2 null mutant) cells were cultured in Dulbecco's Modified Eagle's Medium (DMEM) supplemented with 10% fetal bovine serum (FBS). HeLa, Human Embryonic Kidney (HEK) 293 and HEK293T cells were purchased from ATCC, and cultured in DMEM supplemented with 10% FBS. LNCap and PC3 cells were purchased from ATCC and cultured in DMEM F12 medium supplemented with 10% FBS. RWPE1 and RWPE2 were purchased from ATCC and cultured in keratinocytes-SFM plus supplements medium (Gibco). Primary mammary epithelial (4A100) cultures were derived from organoids isolated from discarded mammary tissue acquired from patients undergoing reduction mammoplasty surgery. Anonymized specimens were acquired from patients who had given written consent, through the Tissue Procurement and Histology Core Facility of the Case Comprehensive Cancer Center (Case CCC), under a Case CCC IRB approved protocol. Primary epithelial cultures were grown in M87A+X medium. Human HME1 cells (Clontech) were grown in medium 171 with mammary epithelial growth supplement (Cascade Biologics) and penicillin-streptomycin. 42 Human breast cancer cell line MDA-MD468 was cultured in RPMI, 5% FBS, supplemented with L-glutamine, penicillin-streptomycin and fungizone (Gibco). Human megakaryocytic cell line DAMI cells was cultured in Iscove's Modified Dulbecco's Medium (IMDM) supplemented with 10% horse serum. Human umbilical vein endothelial cells (HUVEC) were cultured in endothelial cell growth medium with supplements (EGM®-2-Endothelial Cell Medium-2-Lonza).

Transfection

Cells were cultured overnight in DMEM supplemented with 10% FBS. The transfections were performed using SUPERFECT® (Qiagen, Valencia, Calif.) in accordance with the manufacturer's instructions. Transfection efficiency was analyzed by the expression of the EGFP-tagged proteins.

Lentivirus

Five *E. coli* clones expressing pLKO1-shRNA IFNγR2 plasmids were purchased from Open Biosystems (cat #RHS4533-NM_005534). Lentiviruses were produced in HEK293T cells by transfection using each of pLKO1-shRNA IFNγR2, pCMV DR 8.76 and pMD2G. Viruses were produced and used to infect HeLa cells with a 1:3 dilution of stock lentivirus for 16 h. Cells were then cultured for 24 h in complete medium, and then stable clones expressing the shRNA against IFNγR2 and shRNA against GFP (control shRNA) were selected using puromycin. To select the best shRNA targeting IFNγR2 mRNA, cell lysates were analyzed by western blotting, and the best cloneshowing the lowest IFNγR2 protein expression was used to determine the effects of IFNγR2 knock-down in HeLa cells.

Apoptosis Detection

Apoptosis was induced by transfecting the cells with pcDNA3-human Bax, or pcDNA3-human Bak, or pcDNA3-human Bim EL, or by treatment with etoposide (10 µM) or staurosporine (100 nM). To determine the induction of apoptosis by different apoptotic stresses, cells were stained with Hoechst 33258 dye, and the numbers of cells with apoptotic nuclei were counted using fluorescence microscopy. Three hundred cells were analyzed in triplicate samples. The data presented in the figures showed the percentage of apoptosis ±SEM of three independent experiments. Caspase activity were measured by using a fluorogenic caspase 3 substrate II (Calbiochem), IFNγR2 constructs were cloned in pEGFP-C2 (IFNγR2wild type, IFNγR2$_{1-295}$ and IFNγR2$_{296-337}$) vector.

Apoptosis Induction by Overexpression of Bax, Bak or Bim

For Bax, Bak or Bim EL overexpression, cells were transfected with either 1 µg pcDNA3-human Bax, 1 µg pcDNA3-human Bak, or 1 µg pcDNA3 human Bim EL, and 4 µg of pEGFP plasmid encoding IFNγR2, and the apoptosis or caspase activity was determined 24 h after the transfection.

Immunoprecipitations

IFNγR2-Bax Co-Immunoprecipitation (Co-IP)

HEK293T cells were lysed in 300 µl NP40 buffer (150 mM NaCl, 10 mM HEPES at pH 7.4 and 1% NP40) or CHAPS buffer (150 mM NaCl, 10 mM HEPES at pH 7.4 and 1% CHAPS) supplemented with protease inhibitors (1:100 dilution of protease inhibitor Cocktail; Sigma) and PMSF. Samples were pre-cleared by incubating 300-µl (1,000 mg total protein) cell lysates with 20 µl protein-G-sepharose (Amersham Biosciences) at 4° C. for 1 h. Then, the samples were incubated with 20 µl protein-G-sepharose pre-absorbed with 2 µg of Bax monoclonal antibody (B9, Santa Cruz) or IFNγR2 monoclonal antibody (Fitzgerald) at 4° C. for 2 h. After the incubation, sepharose beads were washed with lysis buffer. Beads were then boiled in 30 µl Laemmli buffer, and 15 µl of the sample was analyzed by western blotting. Western blotting analysis of pre-immunoprecipitation (Input) (100 µg total protein) and immunoprecipitated samples (IP) were performed with a Bax monoclonal antibody (B9 antibody, Santa Cruz), Bax polyclonal antibody (N20 antibody, Santa Cruz), or IFNγR2 polyclonal antibody (Fitzgerald).

Binding of Recombinant Proteins

Recombinant human Bax ΔTM (Bax C terminal transmembrane truncated human Bax) was produced by using pHMTc vector downstream of maltose binding protein (MBP), separated by the TEV protease site. Overexpressed MBP-Bax was purified through a maltose-binding column (NEB) and subsequently cleaved by TEV protease (Invitrogen), followed by Ni-affinity purification to remove the protease and the His-tagged MBP. IFNγR2 cytoplamic domain (amino acids 263 337) was fused with thioredoxin (rTrx) to increase the recovery rate from bacterial lysates. The production and the purification of this fusion protein were performed by Protein X Laboratory (San Diego, Calif.). Recombinant Bax (25 ng) was loaded onto Sepharose G beads pre-equilibrated with anti-Bax antibody (Bax B9, Santa Cruz) or pre-immune IgG (control IgG) at 4° C. for 2 h. The excess Bax molecules were washed 3 times with buffer (50 mM phosphate buffer, pH 7.4). Recombinant IFNγR2 (263-337)-rTrx (25 ng) was added to the beads preloaded with Bax and anti-Bax or control IgG. Beads and IFNγR2$_{263-337}$-rTrx were incubated at 4° C. for 2 h. After the incubation, beads were extensively washed with the loading buffer (50 mM phosphate buffer, pH 7.4). Beads were boiled in Laemmli buffer, and the supernatant was collected as a sample. Samples were analyzed by western blot using anti IFNγR2 antibody (C20, Santa Cruz) and Bax (N20, Santa Cruz).

Determination of the Effects of Bcl-2 and BIP on IFNγR2-Bax Interaction

HEK293T cells were lysed by using either NP40 buffer (150 mM NaCl, 10 mM HEPES at pH 7.4 and 1% NP40) or CHAPS buffer (150 mM NaCl, 10 mM HEPES at pH 7.4 and 1% CHAPS) supplemented with protease inhibitors (1:100 dilution of protease inhibitor Cocktail; Sigma) and PMSF, as previously reported. 14 To determine if recombinant Bcl-2 (Prospect cat # PRO-630) protein competes with endogenous IFNγR2 for binding to endogenous Bax, HEK293T cell lysate prepared in NP40 buffer was used. Three-hundred microliters (1,000 µg total protein) of the sample was pre-cleared by incubating in 20 µl protein G-sepharose (Amersham Biosciences) at 4° C. for 1 hour.

Cleared samples (300 µl) were incubated (4° C. for 2 h) with or without recombinant Bcl-2 (75 or 150 nM final concentration) in the presence of protein G sepharose (20 µl) preabsorbed with 2 µg of Bax polyclonal antibody (BD Biosciences). Beads were washed and then boiled in 30 µl Laemmli buffer, and 15 µl of the eluted protein solution was analyzed by western blotting. Western blotting of pre-immunoprecipitation (pre-treated) (100 µg total protein) and immunoprecipitated samples (IP) were performed with IFNγR2 monoclonal antibody (Fitzgerald-WB), Bcl-2 monoclonal antibody (Santa Cruz), and Bax polyclonal antibody (HRP-conjugated N20 antibody, Santa Cruz). To determine the effects of BIP15 on the interaction of endogenous IFNγR2 and Bax, HEK293T cell lysate prepared in CHAPS buffer was used. Three hundred microliters of the sample was pre-cleared by incubating with 20 µl protein G-sepharose (Amersham Biosciences) at 4° C. for 1 h. Cleared samples (300 µl, 1,000 µg total protein) were incubated (37° C. for 2 h) with or without BIP (40 or 200 µM final concentration) in the presence of protein G sepharose (20 µl) preabsorbed with 2 µg of FNγR2 monoclonal antibody (Fitzgerald). Beads were washed and then boiled in 30 µl Laemmli buffer, and 15 µl of the eluted protein solution was analyzed by western blotting. Western blot analysis of Bax was performed by using Bax polyclonal antibody (N20, Santa Cruz).

Inhibition of Bax Activation by IFNγR2

HeLa cells were transiently transfected with pEGFP-C2-IFNγR2 (wild type 1-295, or 296-337) using SUPERFECT® (Qiagen, Valencia, Calif.) in accordance with the manufacturer's instructions. Four micograms of the plasmid were used to transfect cells cultured in 6-cm diameter dishes. After 24 h of transfection, the cells were treated with staurosporine (100 nM) for 3 h. Then, the cells were washed with phosphate buffer pH 7.4 (PBS), fixed using paraformaldehyde (1%), permeabilized with Triton X-100 (0.02%), blocked with goat serum, and the activation of Bax was analyzed by immunocytochemistry using monoclonal Bax 6A7 antibody (BDP-harmingen) and ALEXA FLUOR® 568-labeled anti-mouse IgG secondary antibody (Invitrogen).

Determination of Concentrations of Endogenous IFNγR2 and Bax in Cultured Cells

Recombinant BaxΔTM and IFNγR2263-337-rTrx were used as standards. Cells were harvested and lysed in NP40 buffer (10 mM HEPES, 150 mM NaCl and 1% NP40 pH 7.4), or with hypotonic buffer for subcellular fractionation (20 mM HEPES, 10 mM KCl, 1.5 mM $MgCl_2$, 1 mM EDTA and 250 mM sucrose); both buffers were supplemented with protease inhibitors cocktail (Sigma) and PMSF (Sigma). LDH, F1α and YY1 proteins were used as makers of the cytosolic, mitochondrial and nuclear fractions, respectively. Cell lysates from equivalent cell numbers, and sequential dilutions of protein standards were subjected to SDS-PAGE (BioRad). Bax antibody conjugated with horseradish peroxidase (HRP) (anti-Bax N20-HRP, Santa Cruz) was used to detect Bax, and IFNγR2 antibody (C-20, Santa Cruz) was used to detect IFNγR2. HRP-conjugated anti-rabbit goat IgG was used as a secondary antibody. Signal intensities were analyzed by using BioRad Gel Doc and Quantity One 4.5.1 software from BioRad.

Protein Identification by Mass Spectrometry

To enrich for the immunoreactive (ir) IFNγR2 fragment expressed in transformed cells, DAMI and HEK293T cell lysates were incubated with anti-IFNγR2 antibody (C-20, Santa Cruz) overnight at 4° C., and the antibody-protein complexes were recovered by incubation of the mixture with protein G sepharose. The sepharose gels were then boiled in 30 μl Laemmli buffer, and 15 μl of the eluted protein solution was used for 1D-SDS-PAGE and western analysis. From a Coomassie blue-stained Tris-HCl gel, bands running between the protein markers for 10 and 15 kDa were collected. Proteins were reduced by DTT, alkylated by iodoacetamide and digested by trypsin overnight. The tryptic peptides were extracted from the gel by using 60% acetonitrile in 0.1% formic acid. Recombinant Trx-tagged IFNγR2$_{263-337}$ was used as positive control for the LC-MS/MS analysis. The tryptic peptides were analyzed by LC-MS/MS using a LTQ Orbitrap XL linear ion trap mass spectrometer (Thermo Fisher Scientific, Waltham, Mass.) coupled to an Ultimate 3000 HPLC system (Dionex) in the Case Center for Proteomics. The LC-MS/MS analysis was performed as follows: peptide solutions were injected into a reverse phase Aclaim Pep-Map 100 C18 column (3 mm, 100 Å, 150 mm×75 mm, Dionex Corporation, Sunnyvale, Calif.). Mobil phases used were: 2% acetonitrile, 0.1% formic acid in water (solvent A), and 80% acetonitrile, 0.1% formic acid (solvent B). A linear gradient of solvent B from 0% to 60% over a period of 60 min was used at a flow rate of 300 nL/min. Three specific peptide ions that are expected to be produced from IFNγR2 were selected with a mass window of 3 amu and subjected to MS/MS analysis with a normalized collision energy of 35%. These ions were: m/z 670.4 ($z=2$, DPTQPILEALDK (SEQ ID NO: 11)), 868.9 ($z=2$, DDVWDSVSIISFPEK (SEQ ID NO: 12)), and 754.4 ($z=3$, YWFHTPPSIPLQIEEYLK (SEQ ID NO: 13)). LTQ injection time was set to 2 s and automatic gate control target was 10,000 ions. The results from the LC-MS/MS analysis were subjected to an NCBI nr (version 20070216, containing 4626804 sequences) database search using Mascot Daemon Version 2.2.0 with a mass toleranceset to 2 Da for the precursor and 1 Da for the product ions. In addition to the targeted analysis, the remaining digest was also analyzed by data-dependent LC MS/MS.

The Cytoplasmic C-Terminal Portion of IFNγR2 is a Bax Inhibitor

To perform a yeast-based functional screen for Bax inhibitors, yeast expression cDNA libraries were generated from purified mRNAs of human HeLa cells and mouse brain tissue using pJG4-5 and pYES2 vectors, respectively. As previously reported, two clones encoding the C-terminus of Ku70 were found as Bax suppressors in this screening (FIG. 1A). In the same experiment we also obtained a clone from the HeLa cell library encoding the cytoplasmic domain of IFNγR2 (IFNγR2$_{263-337}$; amino acids 263-337 of IFNγR2) (FIGS. 1A and B) as a Bax suppressor. IFNγR2$_{263-337}$ contains a Jak2-binding domain (amino acids 284-295). To determine the role of the Jak2-binding domain in Bax inhibition, two IFNγR2 mutants were generated (FIG. 1B) and tested for their anti-Bax activity in human cells as described below. One mutant, IFNγR2$_{296-337}$, encodes amino acids 296-337 of IFNγR2 and does not contain the Jak2-binding domain; the other mutant, IFNγR2$_{1-295}$, encodes amino acids 1-295, retaining the Jak2-binding domain but not the C-terminal 41 amino acids of the receptor subunit.

IFNγR2 inhibits Bax-mediated apoptosis. IFNγR2$_{296-337}$ as well as IFNγR2wild type were able to inhibit apoptosis induced by Bax overexpression in HEK293 cells (FIG. 2A). On the other hand, IFNγR2$_{1-295}$ could not protect cells from Bax (FIG. 2A). These results suggest that the Bax-inhibiting domain localizes to the 41 amino acid sequence of the C-terminus of IFNγR2, and that Jak2-STAT1 signaling activated by IFNγ is not necessary for Bax inhibition. To confirm that IFNγR2 does not require Jak2-mediated signaling for Bax inhibition, human cell lines lacking IFNγR2 and Jak2were examined. These cell lines were derived from the HT1080 human fibrosarcoma cell line. In these experiments, etoposide, a DNA topoisomerase II inhibitor, was used to induce apoptosis because etoposide is known to activate the Bax-mediated intrinsic cell death pathway. IFNγR2$_{296-337}$ and IFNγR2wild type were both able to inhibit etoposide-induced apoptosis in these cells, but IFNγR2$_{1-295}$ could not (FIG. 2B-E). These results support the hypothesis that IFNγR2 can rescue cells from apoptosis independent of Jak2-mediated signal transduction.

IFNγR2 Knock-Down Increases Apoptosis in HeLa Cells

To determine whether endogenously expressed IFNγR2 has a physiological role in suppressing apoptosis, IFNγR2 was knocked down by shRNA. HeLa cells were transfected with lentivirus that expresses shRNA targeting IFNγR2 mRNA. HeLa cells transfected with empty vector (pLKO1) or an shRNA targeting GFP mRNA were used as controls (FIG. 3A). IFNγR2 knock-down increased the sensitivity of HeLa cells to etoposide-induced apoptosis (FIG. 3B). Importantly, the basal level of apoptosis was also increased by IFNγR2 knock-down (FIG. 3A). These results suggest that IFNγR2 has a significant role in determining the cell-death sensitivity in HeLa cells.

IFNγR2 Inhibits Apoptosis Induced by Bim but not Bak

Bim is a BH3-only protein, which triggers Bax-mediated apoptosis. IFNγR2wild type as well as IFNγR2$_{296-337}$ were able to inhibit apoptosis induced by Bim overexpression (FIG. 4A). This result suggests that IFNγR2 is able to suppress Bim-dependent Bax activation. On the other hand, IFNγR2 could not rescue cells from apoptosis induced by Bak overexpression (FIG. 4B), suggesting that IFNγR2 specifically inhibits Bax-mediated apoptosis.

Subcellular Localization of IFNγR2-GFP

FIG. 5 shows HeLa (FIGS. 5A-H) and HEK293 (FIGS. 5I and J) cells expressing IFNγR2-GFP fusion proteins. IFNγR2wild type-GFP was detected in the plasma membrane, cytosol and a mitochondrion-like structure (FIGS. 5C, D, I and J) as previously reported. In HeLa cells expressing IFNγR2wild type-GFP, GFP signal was detected mostly in the cytosol and plasma membrane (FIGS. 5C and D), though a weak punctate pattern of GFP signal suggestive of mitochondrial localization was also detected (the image of this pattern was very difficult to capture due to the strong GFP fluorescence in the cytosol and plasma membrane). In the case of HEK293 cells, IFNγR2wild type-GFP localized to a more definite mitochondrionlike structure that was captured in the image (FIGS. 5I and J).

IFNγR2$_{296-337}$-GFP was detected in the cytosol of both HeLa (FIG. 5E and F) and HEK293 cells (not shown). IFNγR2$_{1-295}$-GFP was detected in the cytosol, plasma membrane and the mitochondria-like structures in HeLa (FIG. 5G and H) and HEK293 cells (not shown). In HeLa cells, GFP signal from the mitochondria-like structure was more evident in cells expressing IFNγR2$_{1-295}$-GFP than cells expressing IFNγR2wild type-GFP (FIG. 5C, D and K).

Western Blot Analysis of IFNγR2-GFP

IFNγR2-GFP expression in IFNγR2-null (mutant HT1080) cells was determined by western blot analysis using GFP antibody (FIG. 6A). Estimated molecular weights of IFNγR2wild type-GFP, IFNγR2$_{1-295}$-GFP and IFNγR2$_{296-337}$-GFP, are approximately 67 kDa, 64 kDa and 34 kDa, respectively. Proteins that have similar molecular weights were detected by GFP antibodies (FIG. 6A), suggesting that IFNγR2-GFP were expressed in these cells. Interestingly, we observed that IFNγR2$_{1-295}$-GFP migrated slower than IFNγR2wild type-GFP in every western blotting experiment performed in this study (FIGS. 5A and C). Since the estimated molecular weight of IFNγR2$_{1-295}$-GFP is smaller than IFNγR2wild type-GFP, this observation was unexpected. At present, we do not know the exact reason for this phenomenon, but a posttranslational modification such as glycosylation may be the cause of the slower migration of this mutant protein in SDS-PAGE.

Western blot analysis of IFNγR2-GFP expression was also performed using HEK293 cells (FIG. 6B-D). Although IFNγR2$_{296-337}$-GFP was detected at its estimated molecular weight (FIG. 6B), IFNγR2wild type-GFP and IFNγR2$_{1-295}$-GFP could not be detected in a simple western blot using GFP antibodies in HEK293 cell lysates. To verify the expression of IFNγR2-GFP fusion proteins (both wt and mutants), cell lysates were subjected to GFP immunoprecipitation and samples were further analyzed by IFNγR2 antibodies (FIGS. 6C and D). After enrichment of the GFP-tagged proteins, expression of IFNγR2wild type-GFP and IFNγR2$_{1-295}$-GFP was confirmed by monoclonal antibody recognizing the N-terminus of IFNγR2 (FIG. 6C), and IFNγR2$_{296-337}$-GFP expression was confirmed by antibodies detecting the C-terminus of IFNγR2-GFP (FIG. 6D).

There were GFP-antibody-positive bands with slightly higher and lower molecular weight than GFP (29 kDa) in cells transfected with pEGFP C2-IFNγR2wild type and pEGFP C2-IFNγR2$_{1-295}$ (bands marked with * in FIGS. 6A and B). We speculate that protease-dependent cleavage of IFNγR2-GFP fusion proteins produced these fragments. Protease inhibitors were present in the cell lysis buffer; therefore, it is likely that this cleavage occurred in the cells prior to preparation of the cell lysate, though further careful study will be needed to reveal the reasons for the appearance of these bands.

IFNγR2 Inhibits Bax Activation

Bax activation involves exposure of the protein's N-terminus by a conformational change followed by Bax translocation from the cytosol to mitochondria. Exposure of the N-terminus of Bax can be monitored by immunohistochemistry using 6A7 Bax monoclonal antibody (6A7 Ab) recognizing an epitope in the N-terminus of Bax. Staurosporine (STS), a pan-kinase inhibitor, 30 was used to induce the Bax conformational change. STS treatment (100 nM, 3 h) induced Bax activation that was detected by 6A7 Ab as shown in FIG. 7A. GFP expression itself did not inhibit Bax activation (FIG. 7A). IFNγR2$_{296-337}$-GFP as well as IFNγR2wild type-GFP (FIGS. 7C and D) inhibited STS-induced Bax activation. On the other hand, IFNγR2$_{1-295}$-GFP did not inhibit Bax activation (FIG. 7B). The percentages of 6A7 Ab-positive cells in GFP-positive cells were calculated and the results are shown in FIG. 7E. The inhibition of Bax activation by IFNγR2$_{296-337}$-GFP as well as IFNγR2 wild type-GFP was statistically significant (FIG. 7E).

IFNγR2 Directly Interacts with Bax

To examine whether IFNγR2 can bind Bax, we performed co-immunoprecipitation of endogenously expressed Bax and IFNγR2 in HEK293T cells (FIG. 8). It is known that certain detergents such as NP40 artificially activate Bax whereas CHAPS does not. Interestingly, Bax and IFNγR2 were co-immunoprecipitated by anti-Bax antibody in buffers containing either NP40 or CHAPS (FIG. 8A). This interaction was also observed when anti-IFNγR2 was used for immunoprecipitation and anti-Bax was used for Bax detection in western blot (FIG. 8B). Furthermore, the direct interaction of purified recombinant proteins of BaxΔTM (in which the c-terminal transmembrane (TM) domain is deleted) and IFNγR2$_{263-337}$ (tagged with thioredoxin (rTrx)) was confirmed. These results suggest that the C-terminus of IFNγR2 directly binds Bax.

Bcl-2 Competed with IFNγR2 to Bind Bax In Vitro

Since it is known that Bcl-2 binds and inhibits Bax, we examined whether Bcl-2 has any influence on the IFNγR2-Bax interaction in vitro. Interestingly, addition of recombinant Bcl-2 protein (a truncated form without the C-terminal transmembrane domain to increase solubility in the buffer) to the HEK293T cell lysate interferes with the interaction of Bax and IFNγR2. In this experiment, NP40-based buffer was used because the Bcl-2-Bax interaction is known to be observed in this buffer. This result suggests that Bcl-2 and IFNγR2 recognize the same domain of Bax. We also examined the effects of Bax inhibiting peptide (BIP) designed from the Bax-binding domain of Ku70. Because Ku70 and BIP are known to bind the inactive form of Bax in CHAPS-based buffer, we used CHAPS-based buffer to examine the effects of BIP. As shown in FIG. 8E, BIP did not cause a significant inhibition of the Bax-IFNγR2 interaction. Three independent experiments were performed, and we observed results similar to that in FIG. 8E in two of the experiments. In one experiment, BIP caused a detectable reduction in the amount of IFNγR2 protein pulled down by Bax antibody (data not shown); however, this effect was not reproducible.

Expression of Cytoplasmic IFNγR2 in Transformed Cell Lines

IFNγR2C20 antibody (C20 Ab) recognizes the C-terminal 20 amino acids of IFNγR2 as an epitope. This antibody-detected a small fragment (approximately 10 kDa) in western blot analysis of cell lysates prepared from megakaryocytic cancer cells (DAMI) and SV40-transformed kidney cells (HEK293T), but not from normal primary cultured cells (HUVECs) (FIG. 9A). This small fragment was enriched by immunoprecipitation (FIG. 9B), digested by trypsin and its identity was determined by targeted LC-MS/MS analysis. As a result, it was confirmed that a tryptic peptide derived from the C-terminus of IFNγR2, DPTQPILEALDK (SEQ ID NO: 11), was present in the sample. Expression of this C-terminal fragment was also detected in two cancer cell lines, MDA-MD468 (breast cancer cell line) and PC3(prostate cancer cell line) (FIG. 9C). Interestingly, the C-terminal fragment of IFNγR2was not detected in normal mammary epithelial cells (4A100) or in non tumorigenic immortalized breast (HME-1) and prostate (RWPE-1) cells. These results suggest that a certain protease expressed in malignant tumorigenic cells may produce the antiapoptotic cytoplasmic fragment derived from IFNγR2.

Intracellular Concentrations of IFNγR2 and Bax

The approximate intracellular protein concentrations of IFNγR2 and Bax were determined by densitometric analysis of western blots using purified recombinant proteins as standards (FIGS. 10A and B). For IFNγR2, densitometric analysis was performed on a band corresponding to non-glycosilated full-length INFγR2 (approximately 37 kDa). For Bax, the density of a band corresponding to the full length of Bax (approximately 21 kDa) was measured. As there are other forms (glycosylated, truncated, etc.) of IFNγR2 and Bax, the estimated protein concentration in this experiment may underestimate the actual total expression levels of these proteins in cells.

However, our attempt to obtain an estimate of the stoichiometry of Bax and IFNγR2 will help determine our working hypothesis of how IFNγR2 regulates Bax-mediated apoptosis in the cell. First, the concentrations of Bax and IFNγR2 in total cell lysate (i.e., no fractionation) were measured. The ratio of Bax to IFNγR2 was approximately 1:1, 3:1 and 2:1 in HUVECs, DAMIcells and HEK293T cells, respectively. Next, the concentrations of Bax and IFNγR2 in the cytosol, nucleus and heavy membrane (mitochondria-rich fraction) were measured using DAMI cells and HEK293T cells. The Bax:IFNγR2 ratio in the cytosolic fraction was 2:1 and 3.5:1 in DAMI cells and HEK293T cells, respectively. The ratio in the heavy membrane fraction of DAMI cells and HEK293T cells was approximately 1.5:1 and 6:1, respectively. Interestingly, Bax and IFNγR2 were also detected in the nuclear fraction (FIG. 10). Because the nuclear fraction contains ER membranes attached to the cytosolic surface of the nucleus, the estimated concentration of Bax and IFNγR2 in the nuclear fraction is expected to be higher than the actual concentration in the nucleus.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of inhibiting apoptosis of a cell comprising: administering to the cell a therapeutically effective amount of a cell penetrating peptide (CPP) which inhibits apoptosis of the cell, the CPP consisting of about 5 to about 41 amino acids of SEQ ID NO: 1.

2. The method of claim 1, the CPP binding to Bax in the cell and inhibiting Bax induced apoptosis in the cell.

3. The method of claim 2, the CPP apoptosis inhibiting activity being independent of the Jak/Stat signal transduction pathway.

4. The method of claim 2, the CPP suppressing Bim dependent activation but not apoptosis induced by Bak expression in the cell.

5. The method of claim 1, wherein the CPP inhibits Bax activation.

6. The method of claim 1, the CPP being capable of binding to inactive Bax and N-terminus exposed Bax molecules.

7. The method of claim 1, the peptide comprising PILEA (SEQ ID NO: 2).

8. The method of claim 1, the CPP comprising about 5 to about 10 amino acids and including SEQ ID NO:2.

9. The method of claim 1, the CPP consisting essentially of SEQ ID NO: 2.

10. The method of claim 1, wherein the Bax overexpression in the cell is induced by cytotoxic stresses elicited from chemo-and radiotherapy.

11. The method of claim 1 further comprising administering to the cell a Ku70-derived Bax-inhibiting peptide, wherein the Ku70-derived Bax-inhibiting peptide is selected from the group consisting of VPMLKE (SEQ ID NO: 5), VPMLK (SEQ ID NO: 6), PMLKE (SEQ ID NO: 7), VPTLK (SEQ ID NO: 9), and VPALR (SEQ ID NO: 10).

12. The method of claim 1 further comprising administering to the cell a Ku70-derived Bax-inhibiting peptide, the Ku70-derived Bax-inhibiting peptide consisting the following formula:

$X^1PX^2LX^3X^4$ (SEQ ID NO:4), wherein $X^1$ is selected for amino acids with non-polar side chain;

$X^2$ is selected for amino acids with non-polar side chain;

$X^3$ is selected for amino acids with charged polar side chain;

$X^4$ is selected for amino acids with charged polar side chain; and either $X^1$ or $X^4$ may be absent.

13. A method of treating Bax induced apoptosis associated with an apoptotic disease in a subject, comprising:

administering to the subject a therapeutically effective amount of a cell penetrating peptide (CPP) which inhibits Bax induced apoptosis of a cell, the CPP consisting of about 5 to about 41 amino acids of SEQ ID NO: 1.

14. The method of claim 13, the CPP comprising about 5 to about 10 amino acids and including SEQ ID NO:2.

15. The CPP of claim 13, consisting essentially of SEQ ID NO: 2.

16. The method of claim 13 further comprising administering a peptide selected from the group consisting of VPMLKE (SEQ ID NO: 5), VPMLK (SEQ ID NO: 6), PMLKE (SEQ ID NO: 7), VPTLK (SEQ ID NO: 9), and VPALR (SEQ ID NO: 10).

17. The method of claim 13, the apoptotic disease comprising at least one of ischemic disease, stroke, myocardial infarction, and a degenerative disease.

18. The method of claim 13, wherein the Bax induced apoptosis is induced by the administration of one or more anticancer drug(s) or UV/X-ray irradiation to the subject.

* * * * *